United States Patent [19]

Häbich et al.

[11] Patent Number: 5,492,896
[45] Date of Patent: Feb. 20, 1996

[54] PSEUDOPEPTIDES HAVING AN ANTIVIRAL ACTION

[75] Inventors: Dieter Häbich; Michael Matzke; Klaus Frobel; Thomas Henkel; Hartwig Müller; Karl-Heinz Weber; Jürgen Reefschläger; Gert Streissle; Jutta Hansen, all of Wuppertal; Rainer Neumann, Köln; Arnold Paessens, Haan, all of Germany

[73] Assignee: Bayer Aktiengesellschaft, Leverkusen, Germany

[21] Appl. No.: 196,939

[22] Filed: Feb. 15, 1994

[30] Foreign Application Priority Data

Feb. 15, 1993 [DE] Germany .......................... 43 04 453.0
Mar. 10, 1993 [DE] Germany .......................... 43 07 438.3

[51] Int. Cl.$^6$ .............................. A61K 38/00; C07K 5/00; C07K 7/00; C07K 17/00
[52] U.S. Cl. ................. 514/18; 564/91; 564/99; 564/153; 562/405; 562/510; 560/8; 560/128; 514/19; 530/331
[58] Field of Search .............................. 564/91, 99, 153; 562/405, 510; 560/8, 128; 514/18, 19; 530/331

[56] References Cited

U.S. PATENT DOCUMENTS

| 4,666,889 | 5/1987 | Mine et al. ................................ 514/18 |
| 4,929,736 | 5/1990 | Groutas ..................................... 548/341 |
| 5,086,069 | 2/1992 | Klein et al. .............................. 514/399 |

FOREIGN PATENT DOCUMENTS

| 0077029 | 4/1983 | European Pat. Off. . |
| 0488041 | 6/1992 | European Pat. Off. . |
| 2171103 | 8/1986 | United Kingdom . |
| 9214696 | 9/1992 | WIPO . |

OTHER PUBLICATIONS

Chemical Abstracts, vol. 115, Sep. 2, 1991, No. 9, pp. 1/831; CA#92899u: "Synthesis and biological activity of angiotensin II . . .", R. Mohan et al.
Chemical Abstracts, vol. 114, Apr. 29, 1991, No. 17, pp. 1/834; CA#164760w: "Synthesis of proline–valine pseudodipeptidenol lactones . . .", P. E. Reed et al.
Darby, J. Med. Virol. vol. 1 p. 134 (1993).
ASM News, 1990, American Society for Microbiology, "HIV Protease Inhibitors", cover page+p. 368.
Biochemical and Biophysical Research Communications, vol. 163, No. 2, 1989, pp. 980–987; "Synthetic non–peptide inhibitors . . .", J. J. Blumenstein et al.
Chemistry Express, vol. 6, No. 4, pp. 261–264, 1991; "A Convenient Method for the Synthesis of New Optically . . .", H. Danda et al.

Polish Journal of Chemistry, vol. 54 pp. 2329–2336; "Investigation on Coupling Peptides to Aminomethyl Polymers", A. Orlowska et al.
J. Med. Chem., 1990, vol. 33, pp. 2707–2714; "Orally Potent Human Renin Inhibitors Derived from . . .", K. Iizuka et al.
The EMBO Journal, vol. 7, No. 6, pp. 1785–1791, 1988; "Partial purification and substrate analysis of bacterially . . .", J. Hansen et al.
J.C.S. Chem. Comm., 1976, pp. 451–452; "Pyridinium Polyhydrogen Fluoride, a Deprotecting Reagent in Peptide Chemistry", S. Matsuura et al.
J. Org. Chem., 1985, vol. 50, pp. 2198–2200; "Application of the Swern Oxidation to the Manipulation of . . . ", R. E. Ireland et al.
J. Chem. Research, 1988, pp. 62–63; "Peptide Synthesis using the Pyrrole Ring as an Amino Protecting Group", C. Kashima et al.
Short Communication, Agric. Biol. Chem., vol. 41, No. 7, pp. 1313–1314, 1977; "Novel Microbial Alkaline Proteas Inhibitor . . .", S. Murao et al.
Agric Biol. Chem., vol. 42, No. 12, pp. 2209–2215, 1978; "Isolation and Identification of Microorganism, Producing . . .", S. Murao et al.
Agr. Biol. Chem., vol. 43, No. 2, pp. 243–250, 1979; "Purification and Characterization of Crystalline Microbial Alkaline . . .", T. Watanabe et al.
Agric. Biol. Chem., vol. 43, No. 4, pp. 691–696, 1979; "Protease Inhibitors Produced by Streptomyces Libani", S. Oka et al.
The Journal of Antibiotics, vol. 44, No. 9, pp. 1019–1022; "Isolation of Alpha–Mapi from Fermentation Broths during . . .", S. Stella et al., 1991.
Blumenstein et al, Biochem, Biophys. Res Comm. vol. 163 p. 980 (1989).
ASM News vol. 56 p. 368 (Jul. 1990).

*Primary Examiner*—Howard E. Schain
*Assistant Examiner*—Sheela J. Huff
*Attorney, Agent, or Firm*—Sprung Horn Kramer & Woods

[57] ABSTRACT

The invention relates to new pseudopeptides having an antiviral action, oft he general formula (I)

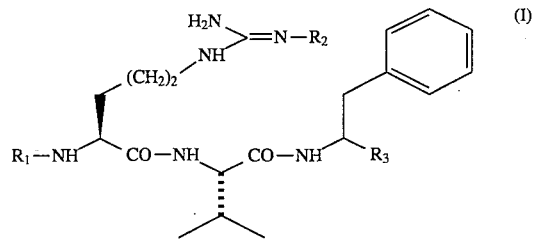

with the meanings given in the description for the substituents, to a process for their preparation and to their use as antiviral agents, in particular against cytomegaloviruses.

9 Claims, No Drawings

PSEUDOPEPTIDES HAVING AN ANTIVIRAL ACTION

The present invention relates to new pseudopeptides having an antiviral action, to a process for their preparation and to their use as antiviral agents, in particular against cytomegaloviruses.

The isolation and characterization of the microbial alkaline protease inhibitor (MAPI) produced by *Streptomyces nigrescens* WT-27 is known from the publications Agric. Biol. Chem. 41, 1313–1314 (1977); 42, 2209–2215, (1978) and 43 (2), 243–250, (1979). It is furthermore known that MAPI can be obtained from fermentation of *Streptomyces libani* S-35 (designation Sp. Chymostatin) [compare Agric. Biol. Chem. 43, 691 (1979)].

An HIV-1 protease-inhibiting action is described for MAPI in the publication J. Antibiot. 44, 1019 (1991). Peptide aldehydes are described as HIV-protease inhibitors in the publication WO 92/14 696.

Various nucleoside and nucleotide analogues, anthraquinone derivatives, cobalt complexes, macrolides and acyl peptides [EP 488 041] are known as classes of compounds having an anti-cytomegalic activity.

The present invention now relates to new pseudopeptides having an antiviral action, of the general formula (I)

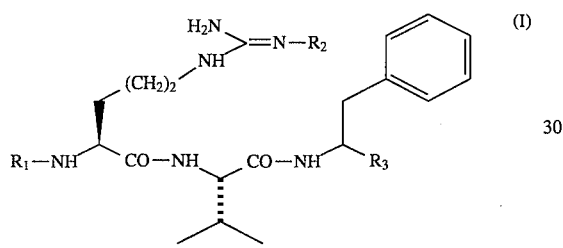

(I)

in which
$R^1$ represents an amino-protective group or represents a radical of the formula $R^4$—NH—CO—,
wherein
$R^4$ denotes cycloalkyl having 3 to 6 carbon atoms, or denotes straight-chain or branched alkyl having up to 18 carbon atoms, which is optionally substituted by hydroxyl, straight-chain or branched alkoxy having up to 4 carbon atoms, halogen, trifluoromethyl, trifluoromethoxy, cycloalkyl having 3 to 6 carbon atoms or by aryl having 6 to 10 carbon atoms, which can in turn be substituted up to twice in an identical or different manner by carboxyl, cyano, hydroxyl, halogen, perhalogenoalkyl having up to 5 carbon atoms or by straight-chain or branched acyl, alkoxy or alkoxycarbonyl having in each case up to 6 carbon atoms, or
alkyl is optionally substituted by a group of the formula —CO $R^5$,
wherein
$R^5$ denotes hydrogen or straight-chain or branched alkyl or alkenyl having in each case up to 8 carbon atoms, which are optionally substituted by phenyl,
or
$R^4$ denotes aryl having 6 to 10 carbon atoms, which is optionally substituted up to 3 times in an identical or different manner by carboxyl, halogen, hydroxyl, cyano, perhalogenoalkyl having up to 5 carbon atoms or by straight-chain or branched acyl, alkoxy, alkoxycarbonyl or vinylalkoxycarbonyl having in each case up to 6 carbon atoms, or
denotes an amino acid radical of the formula

wherein
$R^6$ and $R^7$ are identical or different and denote hydrogen or methyl, or
$R^6$ and $R^7$ together form a 5- or 6-membered saturated carbocyclic ring,
or
$R^6$ denotes hydrogen or methyl
and
$R^7$ denotes cycloalkyl having 3 to 8 carbon atoms or aryl having 6 to 10 carbon atoms or hydrogen, or denotes straight-chain or branched alkyl having up to 8 carbon atoms, the alkyl optionally being substituted by methylthio, hydroxyl, mercapto, guanidyl or by a group of the formula —$NR^9R^{10}$ or $R^{11}$—OC—,
wherein
$R^9$ and $R^{10}$ independently of one another represent hydrogen, straight-chain or branched alkyl having up to 8 carbon atoms or phenyl,
and
$R^{11}$ denotes hydroxyl, benzyloxy, alkoxy having up to 6 carbon atoms or the abovementioned group —$NR^9R^{10}$,
or the alkyl is optionally substituted by cycloalkyl having 3 to 8 carbon atoms or by aryl having 6 to 10 carbon atoms, which is in turn substituted by hydroxyl, halogen, nitro, alkoxy having up to 8 carbon atoms or by the group —$NR^9R^{10}$,
wherein
$R^9$ and $R^{10}$ have the abovementioned meaning,
or the alkyl is optionally substituted by a 5- to 6-membered nitrogen-containing heterocycle or indolyl, wherein the corresponding —NH— functions are optionally protected by alkyl having up to 6 carbon atoms or by an amino-protective group,
$R^8$ denotes straight-chain or branched alkyl having up to 8 carbon atoms, which is optionally substituted by hydroxyl or straight-chain or branched alkoxy having up to 6 carbon atoms, or denotes carboxyl, allyloxycarbonyl, straight-chain or branched alkoxycarbonyl having up to 8 carbon atoms or benzyloxycarbonyl,
$R^2$ represents hydrogen, or represents an amino-protective group, or represents a radical of the formula —$SO_2$—$R^{12}$,
wherein
$R^{12}$ denotes methyl or phenyl, which is optionally substituted up to 4 times in an identical or different manner by methyl or methoxy, or denotes a radical of the formula

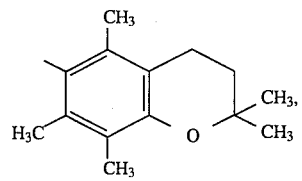

$R^3$ represents formyl or carboxyl or represents straight-chain or branched alkoxycarbonyl having up to 8 carbon atoms or
represents a radical of the formula —$CH_2$—$OR^{13}$ or —$CH(OR^{14})_2$, wherein R[13] and R[14] are identical or different and denote hydrogen, straight-chain or branched alkyl having up to 6 carbon atoms or a hydroxyl-protective group, with the proviso that R[4] may not denote the radical of the formula

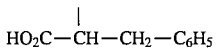

if R[2] represents hydrogen and R[3] represents either formyl or carboxyl, and

R[4] may not denote the radical of the formula

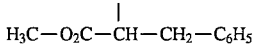

if R[2] represents hydrogen and R[3] represents the —$CH(OCH_3)_2$— group, if appropriate in an isomeric form, and salts thereof.

The compounds of the general formula (I) according to the invention can also be in the form of their salts. Salts with organic and inorganic bases or acids may be mentioned in general here.

The acids which can be added on include, preferably, hydrogen halide acids, such as, for example, hydrofluoric acid, hydrochloric acid and hydrobromic acid, in particular hydrofluoric and hydrochloric acid, and furthermore phosphoric acid, nitric acid, sulphuric acid, mono- and bifunctional carboxylic acids and hydroxycarboxylic acids, such as, for example, acetic acid, maleic acid, malonic acid, oxalic acid, gluconic acid, succinic acid, fumaric acid, tartaric acid, citric acid, salicylic acid, sorbic acid and lactic acid, and sulphonic acids, such as, for example, p-toluenesulphonic acid, 1,5-naphthalenedisulphonic acid or camphorsulphonic acid.

Physiologically acceptable salts can likewise be metal or ammonium salts of the compounds according to the invention which have a free carboxyl group. Particularly preferred salts are, for example, sodium, potassium, magnesium or calcium salts, and ammonium salts which are derived from ammonia or organic amines, such as, for example, ethylamine, di- or triethylamine, di- or triethanolamine, dicyclohexylamine, dimethylaminoethanol, arginine, lysine or ethylenediamine.

A hydroxyl-protective group in the context of the abovementioned definition in general represents a protective group from the series comprising: tert-butoxydiphenylsilyl, trimethylsilyl, triethylsilyl, triisopropylsilyl, tert-butyl-dimethylsilyl, tert-butyldiphenylsilyl, triphenylsilyl, trimethylsilylethoxycarbonyl, benzyl, benzyloxycarbonyl, 2-nitrobenzyl, 4-nitrobenzyl, 2-nitrobenzyloxycarbonyl, 4-nitrobenzyloxycarbonyl, tert-butyloxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methylthiomethyl, methoxyethoxymethyl, [2-(trimethylsilyl)ethoxy]methyl, 2-(methylthiomethoxy)ethoxycarbonyl, benzoyl, 4-methylbenzoyl, 4-nitrobenzoyl, 4-fluorobenzoyl, 4-chlorobenzoyl and 4-methoxybenzoyl. Acetyl, benzoyl, benzyl and methylbenzyl are preferred.

Amino-protective groups in the context of the invention are the customary amino-protective groups used in peptide chemistry.

These include, preferably: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichloroethoxycarbonyl, 2,2,2-trichloro-tert-butoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl and benzyloxymethylene, 4-nitrobenzyl, 2,4-dinitrobenzyl and 4-nitrophenyl.

As the radical of the general formula (II)

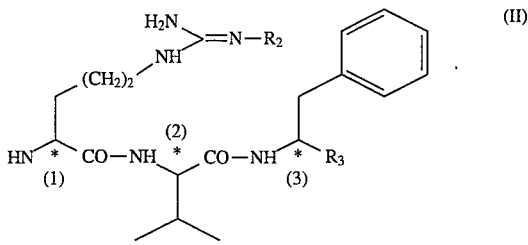

shows, the compounds of the general formula (I) according to the invention have at least 3 asymmetric carbon atoms (*). They can be in the D- or L-form and R- or S-configuration independently of one another. The invention comprises the optical isomers as well as the isomer mixtures or racemates.

The compounds of the general formulae (I) and (Ia) according to the invention can exist in stereoisomeric forms, for example they either behave as mirror images (enantiomers) or do not behave as mirror images (diastereomers), or they are present as a diastereomer mixture. The invention relates both to the antipodes, racemic forms and diastereomeric mixtures and to the pure isomers. The racemic forms, like the diastereomers, can be separated into the stereoisomerically uniform constituents in a known manner [compare E. L. Eliel, Stereochemistry of Carbon Compounds, McGraw Hill, 1962]. The separation into the stereoisomerically uniform compounds is carried out, for example, via chromatographic racemate splitting of diastereomeric esters and amides or on optically active phases. Crystallization of diastereomeric salts is furthermore possible.

Preferred compounds of the general formula (I) are those in which

R[1] represents acetyl, tert-butoxycarbonyl (Boc), benzyloxycarbonyl (Z) or 9-fluorenylmethoxycarbonyl (Fmoc), or represents a radical of the formula R[4]—NH—CO—, wherein R[4] denotes cyclopentyl or cyclohexyl or denotes straight-chain or branched alkyl having up to 16 carbon atoms, which is optionally substituted by hydroxyl, methoxy, fluorine, chlorine, bromine, trifluoromethyl, trifluoromethoxy, cyclopentyl, cyclohexyl or phenyl, which can in turn be substituted up to twice in an identical or different manner by carboxyl, cyano, hydroxyl, fluorine, chlorine, bromine, perhalogenoalkyl having up to 4 carbon atoms or by straight-chain or branched acyl, alkoxy or alkoxycarbonyl having in each case up to 4 carbon atoms, or alkyl is optionally substituted by a group of the formula —CO$_2$R$^5$,
wherein
R$^5$ denotes hydrogen or straight-chain or branched alkyl or alkenyl having in each case up to 6 carbon atoms, which are optionally substituted by phenyl, or R$^4$ denotes phenyl or naphthyl, which is optionally substituted up to 3 times in an identical or different manner by carboxyl, fluorine, chlorine, bromine, hydroxyl, cyano, perhalogenoalkyl having up to 4 carbon atoms or by straight-chain or branched acyl, alkoxy, alkoxycarbonyl or vinylalkoxycarbonyl having in each case up to 5 carbon atoms, or denotes an amino acid radical of the formula

wherein
R$^6$ and R$^7$ are identical or different and denote hydrogen or methyl, or
R$^6$ and R$^7$ together form a cyclopentyl or cyclohexyl ring, or R$^6$ denotes hydrogen or methyl
and
R$^7$ denotes cyclopentyl, cyclohexyl, phenyl or hydrogen, or
denotes straight-chain or branched alkyl having up to 6 carbon atoms, the alkyl optionally being able to be substituted by methylthio, hydroxyl, mercapto, guanidyl, amino, carboxyl or H$_2$N—CO—,
or the alkyl is substituted by cyclohexyl, naphthyl or phenyl, which can in turn be substituted by fluorine, hydroxyl, nitro or alkoxy having up to 4 carbon atoms,
or the alkyl is optionally substituted by indolyl, imidazolyl, pyridyl, triazolyl or pyrazolyl, the corresponding —NH— functions optionally being protected by alkyl having up to 4 carbon atoms or by an amino-protective group,
R$^8$ denotes straight-chain or branched alkyl having up to 6 carbon atoms, which is optionally substituted by hydroxyl or straight-chain or branched alkoxy having up to 4 carbon atoms, or
denotes carboxyl, allyloxycarbonyl, straight-chain or branched alkoxycarbonyl having up to 6 carbon atoms or benzyloxycarbonyl,
R$^2$ represents hydrogen, benzyloxycarbonyl, tert-butoxycarbonyl or
represents a radical of the formula —SO$_2$—R$^{12}$,
wherein
R$^{12}$ denotes methyl or phenyl, which is optionally substituted up to 4 times in an identical or different manner by methyl or methoxy, or denotes a radical of the formula

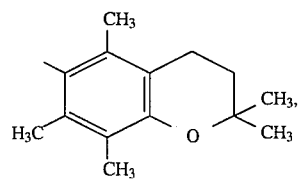

R$^3$ represents formyl or carboxyl or represents straight-chain or branched alkoxycarbonyl having up to 6 carbon atoms, or
represents a radical of the formula —CH$_2$—OR$^{13}$ or —CH(OR$^{14}$)$_2$,
wherein
R$^{13}$ and R$^{14}$ are identical or different and denote hydrogen, straight-chain or branched alkyl having up to 4 carbon atoms, acetyl or benzyl,
with the proviso that
R$^4$ may not denote the radical of the formula

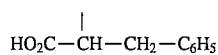

if R$^2$ represents hydrogen and R$^3$ represents either formyl or carboxyl,
and
R$^4$ may not denote the radical of the formula

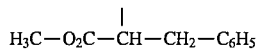

if R$^2$ represents hydrogen and R$^3$ represents the —CH(OCH$_3$)$_2$—, group, if appropriate in an isomeric form, and salts thereof.

Particularly preferred compounds of the general formula (I) are those
in which
R$^1$ represents acetyl, tert-butoxycarbonyl (Boc), benzyloxycarbonyl (Z) or 9-fluorenylmethoxycarbonyl (Fmoc), or
represents a radical of the formula R$^4$—NH—CO—,
wherein
R$^4$ denotes cyclopentyl or cyclohexyl or denotes straight-chain or branched alkyl having up to 14 carbon atoms, which is optionally substituted by hydroxyl, methoxy, fluorine, trifluoromethyl, trifluoromethoxy, cyclohexyl or phenyl, or which is optionally substituted by a group of the formula —CO$_2$R$^5$,
wherein
R$^5$ denotes hydrogen or straight-chain or branched alkyl or alkenyl having in each case up to 4 carbon atoms or benzyl, or R$^4$ denotes phenyl, which is optionally substituted up to twice in an identical or different manner by carboxyl, fluorine, hydroxyl, cyano, trifluoromethyl or by straight-chain or branched acyl, alkoxy, alkoxycarbonyl or vinylalkoxycarbonyl having in each case up to 4 carbon atoms, or
denotes an amino acid radical of the formula

wherein
$R^6$ and $R^7$ are identical or different and denote hydrogen or methyl, or
$R^6$ and $R^7$ together form a cyclohexyl ring,
or
$R^6$ denotes hydrogen or methyl
and
$R^7$ denotes cyclopentyl, cyclohexyl or hydrogen, or denotes straight-chain or branched alkyl having up to 4 carbon atoms,
the alkyl optionally being able to be substituted by methylthio, hydroxyl, mercapto, guanidyl, amino, carboxyl or $H_2N$—CO—,
or the alkyl is substituted by cyclohexyl, naphthyl or phenyl, which can in turn be substituted by fluorine, chlorine or alkoxy having up to 4 carbon atoms,
or the alkyl is optionally substituted by imidazolyl, pyridyl or pyrazolyl, the corresponding —NH— functions optionally being protected by methyl, benzyloxymethylene or tert-butyloxycarbonyl (Boc),
$R^8$ denotes straight-chain or branched alkyl having up to 4 carbon atoms, which is optionally substituted by hydroxyl or straight-chain or branched alkoxy having up to 3 carbon atoms, or
denotes carboxyl, allyloxycarbonyl, straight-chain or branched alkoxycarbonyl having up to 4 carbon atoms or benzyloxycarbonyl,
$R^2$ represents hydrogen or
represents a radical of the formula —$SO_2$—$R^{12}$,
wherein
$R^{12}$ denotes methyl or phenyl, which is optionally substituted up to 4 times in an identical or different manner by methyl or methoxy, or denotes a radical of the formula

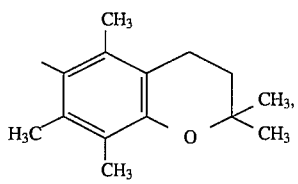

$R^3$ represents formyl or carboxyl or
represents straight-chain or branched alkoxycarbonyl having up to 4 carbon atoms, or
represents a radical of the formula —$CH_2$—$OR^{13}$ or —$CH(OR^{14})_2$,
wherein
$R^{13}$ and $R^{14}$ are identical or different and denote hydrogen, straight-chain or branched alkyl having up to 3 carbon atoms or benzyl,
with the proviso that
$R^4$ may not denote the radical of the formula

if $R^2$ represents hydrogen and $R^3$ represents either formyl or carboxyl, and
$R^4$ may not denote the radical of the formula

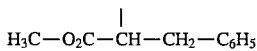

if $R^2$ represents hydrogen and $R^3$ represents the —$CH(OCH_3)_2$— group,
if appropriate in an isomeric form, and salts thereof.

A new process for the preparation of the compounds of the general formula (I) according to the invention has furthermore been found, characterized in that compounds of the general formula (III)

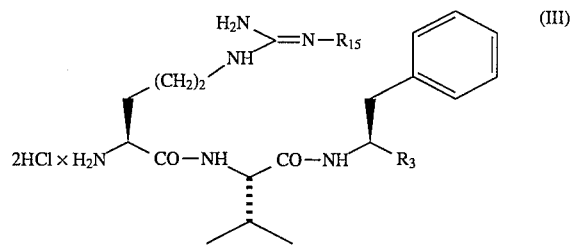

in which
$R^3$ has the abovementioned meaning
and
$R^{15}$ has the abovementioned meaning of $R^2$, but does not represent hydrogen,
are first converted, by reaction with compounds of the general formula (IV)

$$R^4—N=C=O \quad (IV)$$

in which
$R^4$ has the abovementioned meaning,
in inert solvents, in the presence of a base, into the compounds of the general formula (V)

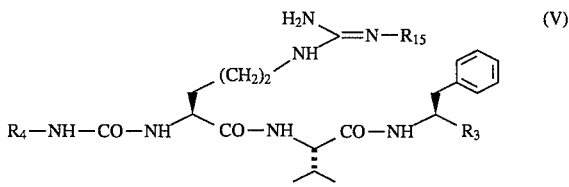

in which
$R^3$ $R^4$ and $R^{15}$ have the abovementioned meaning,
and, in the case where $R^3$=$CH_2$—OH, the compounds of the general formula (V) ($R^3$=$CO_2CH_3$) are reacted by customary methods, but preferably with sodium borohydride,
and, in the case where $R^3$=CHO, the compounds of the general formula (V) are subjected to a Swern oxidation, starting from the hydroxymethyl compound ($R^3$=$CH_2$—OH),
and, depending on the radical $R^{15}$, are reacted, for example, with hydrofluoric acid or trifluoroacetic acid,
and, in the case of an amino-protective group ($R^1$/$R^{15}$), this is split off by the methods customary in peptide chemistry,
and, in the case of the acids, the esters are hydrolysed.

The process according to the invention can be illustrated by way of example by the following equation (equations 1–4):

Equation 1:

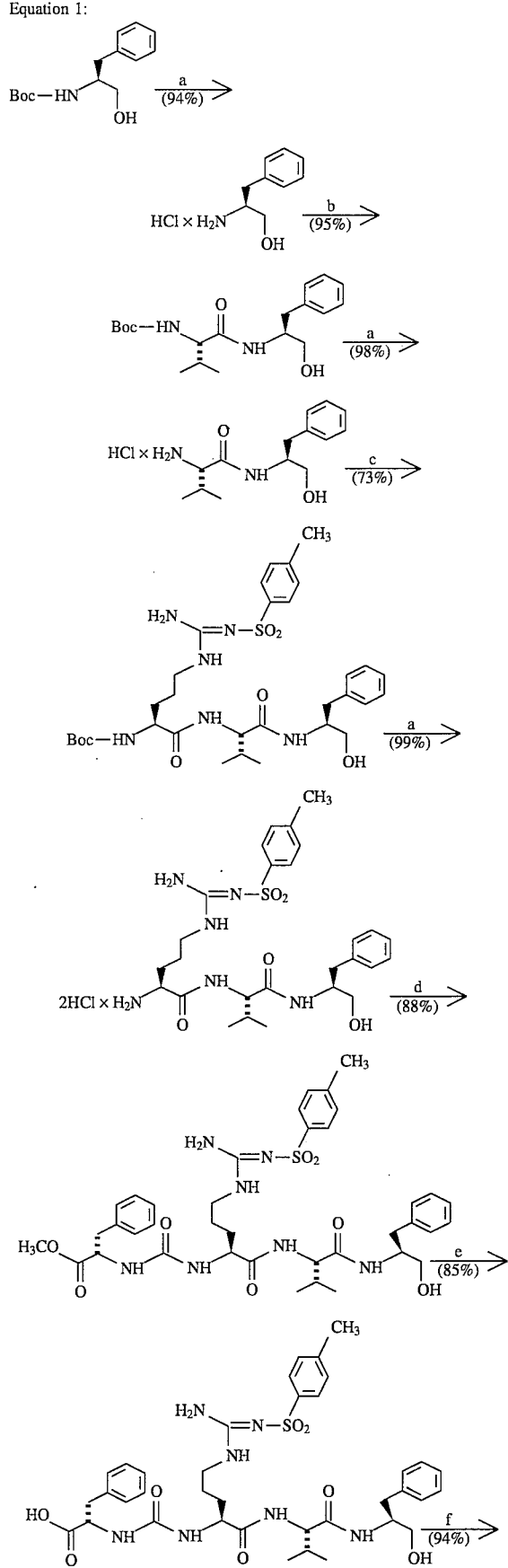

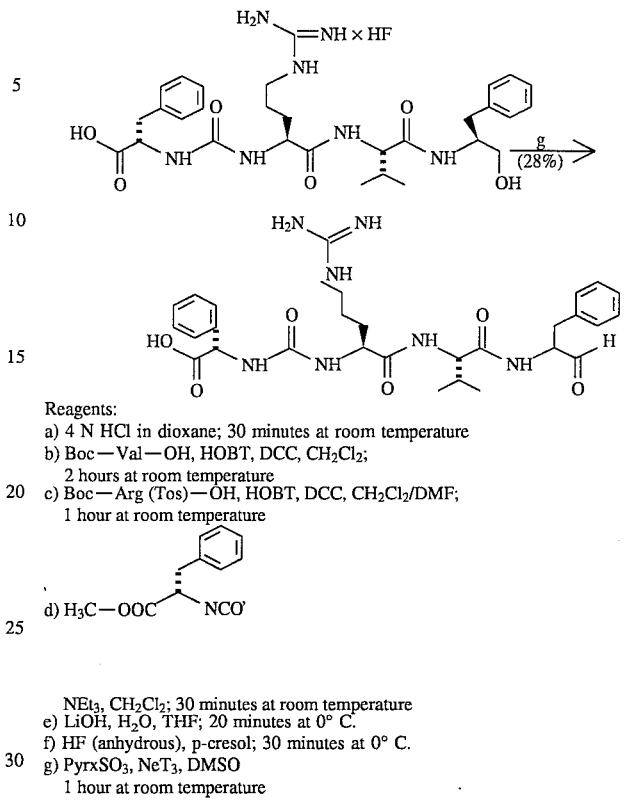

Reagents:
a) 4 N HCl in dioxane; 30 minutes at room temperature
b) Boc—Val—OH, HOBT, DCC, CH$_2$Cl$_2$; 2 hours at room temperature
c) Boc—Arg(Tos)—OH, HOBT, DCC, CH$_2$Cl$_2$/DMF; 1 hour at room temperature
d) H$_3$C—OOC—*—NCO'

NEt$_3$, CH$_2$Cl$_2$; 30 minutes at room temperature
e) LiOH, H$_2$O, THF; 20 minutes at 0° C.
f) HF (anhydrous), p-cresol; 30 minutes at 0° C.
g) PyrxSO$_3$, NEt$_3$, DMSO 1 hour at room temperature Equation 2:

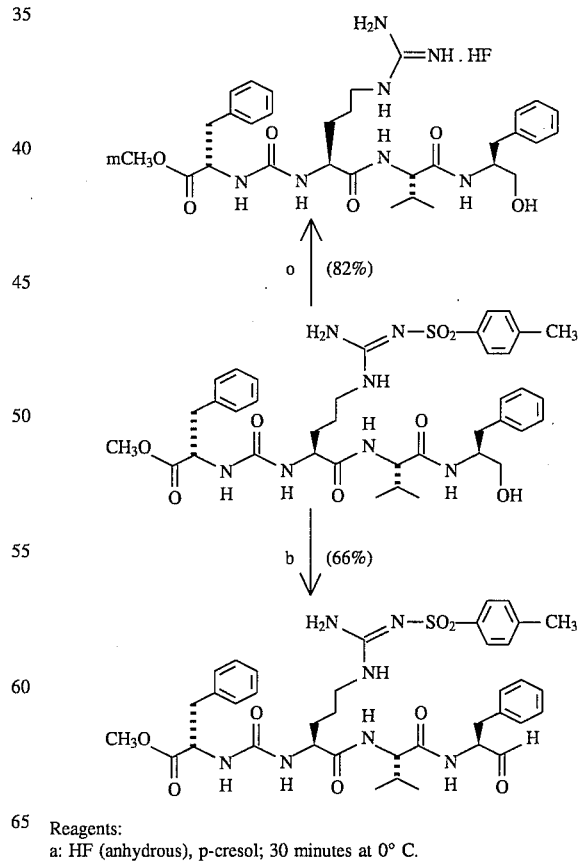

Reagents:
a: HF (anhydrous), p-cresol; 30 minutes at 0° C.

11

-continued b: Pyr SO₃, NEt₃, DMSO; 1 hour at room temperature

Equation 3:

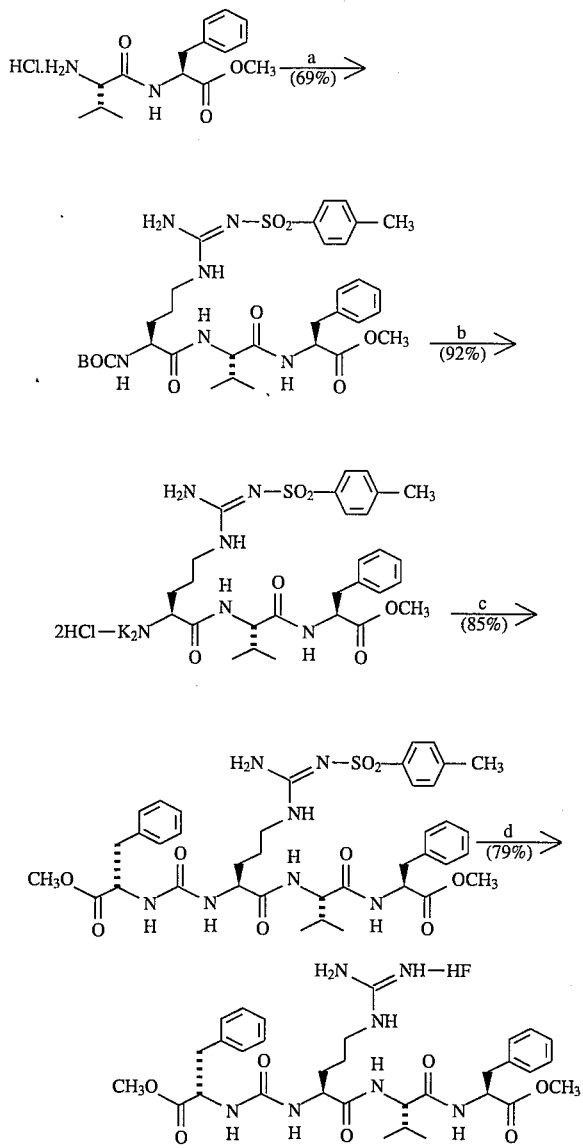

Reagents:

a. Boc—Ar—g(—Tos)—OH, HOBT, DCC, CH₂Cl₂, DMF; 1 hour at room temperature
b. 4N HCl in dioxane; 30 minutes at room temperature
c. CH₃OOC-CH(CH₂Ph)-NCO, NEt₃, CH₂Cl₂; 30 minutes at room temperature
d. HF (anhydrous), p-cresol; 30 minutes at 0° C.
e. LiOH, H₂O, THF; 20 minutes at 0° C.

12

Equation 4:

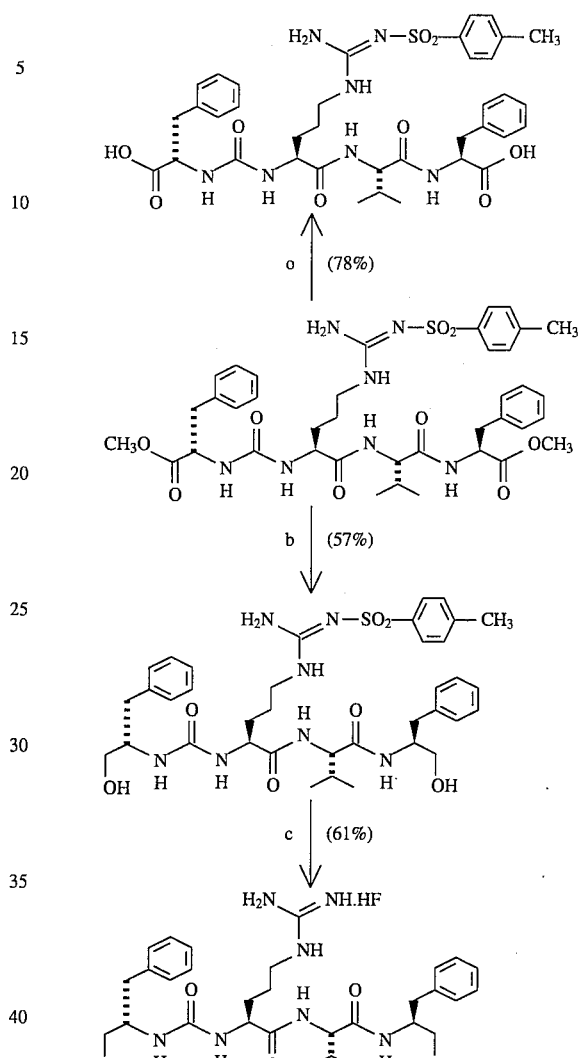

Reagents:
a. LiOH, H₂O, THF; 20 minutes at 0° C.
b. NaBH₄, LiI, THF, MeOH; 5 hours at 40° C.
c. HF (anhydrous), p-cresol; 30 minutes at 0° C.

Suitable solvents for all the process steps are the customary inert solvents which do not change under the reaction conditions. These include, preferably, organic solvents, such as ethers, for example diethyl ether, glycol mono- or dimethyl ether, dioxane or tetrahydrofuran, or hydrocarbons, such as benzene, p-cresol, toluene, xylene, cyclohexane or petroleum fractions, or halogenohydrocarbons, such as methylene chloride, chloroform or carbon tetrachloride, or dimethyl sulphoxide, dimethylformamide, hexamethylphosphoric acid triamide, ethyl acetate, pyridine, triethylamine or picoline. It is also possible to use mixtures of the solvents mentioned, if appropriate also with water. Methylene chloride, tetrahydrofuran, dioxane and dioxane/water are particularly preferred.

Suitable bases are organic amines, such as trialkyl ($C_1$–$C_6$)amines, such as, for example, triethylamine, or heterocycles, such as pyridine, methylpiperidine, piperidine or N-methylmorpholine. Triethylamine and N-methylmorpholine are preferred.

The bases are in general employed in an amount of 0.1 mol to 5 mol, preferably 1 mol to 3 mol, in each case per mole of the compounds of the general formula (III).

The reactions can be carried out under normal pressure, but also under increased or reduced pressure (for example 0.5 to 3 bar). They are in general carried out under normal pressure.

The reactions are carried out in a temperature range from 0° C. to 100° C. preferably at 0° C. to 30° C., and under normal pressure.

The amino-protective groups are split off in a manner which is known per se.

The tosyl group is in general split off with hydrofluoric acid (anhydrous) in the presence of a scavenger, preferably p-cresol, or with pyridinium hydrofluoride [see Matsuura et al., J.C.S. Chem. Comm. (1976), 451], in a temperature range from −10° C. to +30° C., preferably at 0° C.

The carboxylic acid esters are hydrolysed by customary methods by treating the esters with customary bases in inert solvents, it being possible for the salts initially formed to be converted into the free carboxylic acids by treatment with acid.

Suitable bases for the hydrolysis are the customary inorganic bases. These include, preferably, alkali metal hydroxides or alkaline earth metal hydroxides, such as, for example, sodium hydroxide, lithium hydroxide, potassium hydroxide or barium hydroxide, or alkali metal carbonates, such as sodium carbonate or potassium carbonate or sodium bicarbonate, or alkali metal alcoholates, such as sodium ethanolate, sodium methanolate, potassium ethanolate, potassium methanolate or potassium tert-butanolate. Sodium hydroxide or lithium hydroxide is particularly preferably employed.

Suitable solvents for the hydrolysis are water or the organic solvents customary for a hydrolysis. These include, preferably, alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is also possible to employ mixtures of the solvents mentioned. Water/tetrahydrofuran is preferred.

The hydrolysis is in general carried out in a temperature range from 0° C. to +100° C., preferably from 0° C. to +40° C.

The hydrolysis is in general carried out under normal pressure. However, it is also possible to carry it out under reduced pressure or under increased pressure (for example from 0.5 to 5 bar).

In carrying out the hydrolysis, the base or the acid is in general employed in an amount of 1 to 3 mol, preferably 1 to 1.5 mol, per mole of the ester. Molar amounts of the reactants are particularly preferably used.

In carrying out the reaction, the salts of the compounds according to the invention are formed in the first step as intermediate products, which can be isolated. The acids according to the invention are obtained by treatment of the salts with customary inorganic acids. These include, preferably, mineral acids, such as, for example, hydrochloric acid, hydrobromic acid, sulphuric acid, citric acid or phosphoric acid. In the preparation of the carboxylic acids, it has proved advantageous to acidify the basic reaction mixture of the hydrolysis in a second step without isolation of the salts. The acids can then be isolated in the customary manner.

The reductions can in general be carried out by hydrogen in water or in inert organic solvents, such as alcohols, ethers or halogenohydrocarbons, or mixtures thereof, using catalysts, such as Raney nickel, palladium, palladium on animal charcoal or platinum, or with hydrides or boranes in inert solvents, if appropriate in the presence of a catalyst.

The reduction is preferably carried out with hydrides, such as complex borohydrides or aluminium hydrides. Sodium borohydride, lithium aluminium hydride or sodium cyanoborohydride is particularly preferably employed here.

Suitable solvents here are all the inert organic solvents which do not change under the reaction conditions. These include, preferably, alcohols, such as methanol, ethanol, propanol or isopropanol, or ethers, such as diethyl ether, dioxane, tetrahydrofuran, glycol dimethyl ether or diethylene glycol dimethyl ether, or amides, such as hexamethylphosphoric acid triamide or dimethylformamide, or acetic acid. It is also possible to use mixtures of the solvents mentioned. Methanol and tetrahydrofuran are preferred.

Potassium or lithium iodide, preferably lithium iodide, can also be employed as catalysts in the reductions.

The catalyst is in general employed in an amount of 0.1 mol to 5 mol, preferably 1 mol to 3 mol, in each case per mole of the ester to be reduced.

The reaction can be carried out under normal, increased or reduced pressure (for example 0.5 to 5 bar). It is in general carried out under normal pressure.

The reductions are in general carried out in a temperature range from 0° C. to +60° C., preferably at +10° C. to +40° C.

The oxidation of alcohol groups to the corresponding aldehydes is in general carried out in one of the abovementioned solvents in the presence of one of the abovementioned bases using oxidizing agents, such as, for example, potassium permanganate, bromine, Jones reagent, pyridine dichromate, pyridinium chlorochromate, pyridine/sulphur trioxide complex or oxalyl chloride [Swern oxidation (ClCOCOCl/DMSO/CH$_2$Cl$_2$/NEt$_3$), for example in accordance with the method of R. E. Ireland et al., J. Org. Chem. 50, 2199 (1985)]. The oxidation is preferably carried out with pyridine/sulphur trioxide complex in dimethyl sulphoxide in the presence of triethylamine.

The oxidation is in general carried out in a temperature range from 0° C. to +50° C., preferably at room temperature under normal pressure.

The compounds of the general formula (III) are new and can then be prepared by those methods customary in peptide chemistry, for example by a process in which compounds of the general formula (VI)

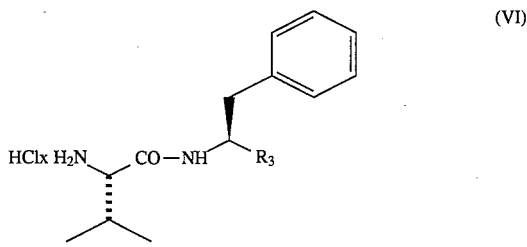

in which

R$^3$ has the abovementioned meaning, are reacted with the amino acid derivatives of the formula (VII)

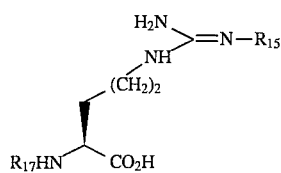

in which

R[15] has the abovementioned meaning and

R[17] represents one of the abovementioned amino-protective groups, preferably 9-fluorenylmethoxycarbonyl (Fmoc), tert-butoxycarbonyl (Boc) or benzyloxycarbonyl, in one of the abovementioned solvents, preferably methylene chloride, in the presence of an auxiliary and/or base, preferably HOBT and dicyclohexylcarbodiimide, and the amino-protective group is then split off, likewise by customary methods, preferably with hydrochloric acid in dioxane.

All the process steps are carried out under normal pressure and in a temperature range from 0° C. to room temperature, preferably at room temperature.

The compounds of the general formulae (VI) and (VII) are known in most cases or can be prepared by customary methods [compare J. Chem. Res., Synop., (2), 62–63; DE 36 04 510].

The compounds of the general formula (IV) are likewise known [compare U.S. Pat. No. 4,929,736].

The compounds display an antiviral action against retroviruses and representatives of the Herpetoviridae group, in particular against human cytomegalovirus (HCMV).

The anti-HCMV action was determined in a screening test system in 96-well microtitre plates with the aid of human embryonal lung fibroblasts (HELF) cell cultures. The influence of the substances on the spread of the cytopathogenic effect was determined in comparison with the reference substance ganciclovir (Cymevene®-sodium), a clinically approved anti-HCMV chemotherapeutic.

The substances are dissolved in DMSO (dimethyl sulphoxide; 50 mM) and investigated on microtitre plates (96-well) in final concentrations of 1000–0.00048 µM (micromolar) in duplicate determinations (4 substances/plate). Toxic and cytostatic actions of the substances are also recorded here. After the appropriate dilutions of the substances (1:2) on the microtitre plate, a suspension of 50–100 HCMV-infected HELF cells and $3\times10^4$ non-infected HELF cells in Eagle's MEM (minimal essential medium) with 10% foetal calf serum is introduced into each cup and the plates are incubated at 37° C. in a $CO_2$ incubating cabinet for 6 days. After this period, the cell lawn in the substance-free virus controls, starting from 50–100 infectious centres, is completely destroyed by the cytopathogenic effect (CPE) of the HCMV (100% CPE). After staining with neutral red and fixing with formalin/methanol, the plates are evaluated with the aid of a projection microscope (Plaque Viewer). The results are summarized in the following table for some of the compounds:

Table: Anti-HCMV (Davis strain) activity and anticellular action

| Ex. No. | $IC_{50}$ (µM)[1] HCMV | $CIC_{50}$ (µM)[2] HELF | $SI^3$ |
| --- | --- | --- | --- |
| 4 | 1.95 | 62.5 | 32 |
| 19 | 0.45 | 15.6 | 35 |
| 43 | 0.45 | 62.5 | 140 |
| 46 | 7.8 | 500 | 64 |
| 54 | 0.06 | 4 | 67 |
| 69 | 0.06 | 15.6 | 260 |
| 56 | 0.24 | 31 | 130 |
| 75 | 0.015 | 3.9 | 260 |
| Cymevene ®-Na 2–4 | 125 | 32 | –64 |

[1] $IC_{50}$ = Concentration of the compound according to the invention which causes 50% inhibition of the CPE.
[2] $CIC_{50}$ = Maximum concentration which displays no evident anticellular action.
3) $SI = \dfrac{CIC_{50}}{IC_{50}}$ = selectivity index It has now been found that the compounds according to the invention inhibit the multiplication of HCMV in HELF cells in concentrations which are sometimes 10–50 times lower than those of Cymevene®-sodium, and have a selectivity index which is several times higher.

The compounds according to the invention are thus valuable active compounds for the treatment and prophylaxis of diseases caused by human cytomegalovirus infections. Fields of indication which may be mentioned are, for example:

1) Treatment and prophylaxis of cytomegalovirus infections in bone marrow and organ transplant patients suffering often potentially fatally from HCMV pneumonitis or encephalitis and gastrointestinal and systemic HCMV infections.

2) Treatment and prophylaxis of HCMV infections in AIDS patients (retinitis, pneumonitis, gastrointestinal infections).

3) Treatment and prophylaxis of HCMV infections in pregnant women, newborn babies and infants.

It has furthermore been found, surprisingly, that the compounds of the general formula (I) have an action against retroviruses. This is documented by an HIV-specific protease enzyme test.

The results of the examples described below were determined by the HIV test system described in the following literature references [compare Hansen, J., Billich, S., Schulze, T., Sukrow, S. and Mölling, K. (1988), EMBO Journal, volume 7, No. 6, pages 1785–1791]: purified HIV protease was incubated with a synthetic peptide which imitates a cutting site in the Gag precursor protein and represents an in vivo cleavage site of HIV protease. The cleavage products formed from the synthetic peptide were analysed by reverse phase high performance liquid chromatography (RP-HPLC). The $IC_{50}$ values stated relate to the substance concentration which causes 50% inhibition of protease activity under the abovementioned test conditions.

TABLE

| | $IC_{50}$ (RP-HPLC) (µM) |
| --- | --- |
| Ex. No. | HIV-1 |
| VIII | 19 |
| IX | 160 |

TABLE-continued

| Ex. No. | IC$_{50}$ (RP-HPLC) (µM) HIV-1 |
|---|---|
| 17 | 1.6 |
| 20 | 0.013 |
| 42 | 0.15 |
| 49 | 0.26 |
| 50 | 0.14 |
| 51 | 2.1 |
| 52 | 12.0 |
| 55 | 0.12 |
| 56 | 0.24 |
| 57 | 1.5 |
| 58 | 0.0018 |
| 82 | 14 |
| 83 | 0.0024 |

The new active compound can be converted in a known manner into the customary formulations, such as tablets, coated tablets, pills, granules, aerosols, syrups, emulsions, suspensions and solutions, using inert, nontoxic, pharmaceutically suitable excipients or solvents.

The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Administration is effected in the customary manner, preferably orally, parenterally or topically, in particular perlingually or intravenously.

In the case of parenteral use, solutions of the active compound can be employed, using suitable liquid excipient materials.

In general, it has proved advantageous in the case of intravenous administration to administer amounts of about 0.001 to 10 mg/kg, preferably about 0.01 to 5 mg/kg of body weight in order to achieve effective results, and in the case of oral administration the dosage is about 0.01 to 25 mg/kg, preferably 0.1 to 10 mg/kg of body weight.

Nevertheless, it may be necessary to deviate from the amounts mentioned, and in particular as a function of the body weight or the nature of the administration route, and of the behaviour of the individual towards the medicament, the nature of its formulation and the time or interval at which administration takes place. Thus, in some cases it may be sufficient to manage with less than the abovementioned minimum amount, while in other cases the upper limit mentioned must be exceeded. Where relatively large amounts are administered, it may be advisable to divide these into several individual doses over the course of the day.

As enzyme inhibitors, the compounds according to the invention can be employed in all fields generally known for inhibitors. By these are meant, for example, use as an affinity label for affinity chromatography for purification of proteases. However, they can also be used as auxiliaries for clarification of reaction mechanisms and for improving the specificity of diagnostic methods.

Appendix to the experimental section

I. Amino acids

The configuration is in general designated by placing an L or D before the amino acid abbreviation, and in the case of the racemate by placing D,L- in front, but, for simplification, the configuration designation may be omitted for L-amino acids and an explicit designation is then given only in the case of the D-form or the D,L mixture.

| | |
|---|---|
| Arg | L-arginine |
| Ile | L-isoleucine |
| Leu | L-leucine |
| Phe | L-phenylalanine |
| Val | L-valine |

II. Abbreviations

| | |
|---|---|
| Z | Benzyloxycarbonyl |
| Boc | tert-butyloxycarbonyl |
| CMCT | 1-cyclohexyl-3-(2-morpholino-ethyl)-carbodiimide metho-p-toluene-sulphonate |
| DCC | Dicyclohexylcarbodiimide |
| DMF | Dimethylformamide |
| HOBT | 1-hydroxybenzotriazole |
| Ph | Phenyl |
| THF | Tetrahydrofuran |
| DMSO | Dimethylsulphoxide |
| Fmoc | 9-fluorenylmethoxycarbonyl |

III. List of the mobile phase mixtures used for the chromatography

| | |
|---|---|
| I: | Methylene chloride: methanol |
| II: | Toluene: ethyl acetate |
| III: | Acetonitrile: water |

STARTING COMPOUNDS

EXAMPLE I (2S)-2-Amino-3-phenyl-propan-1-ol hydrochloride

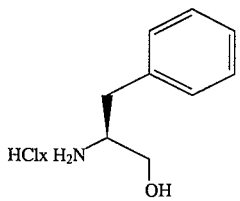

A solution of 20.10 g (80.00 mmol) of (S)-2-(tert-butoxycarbonylamino-1-phenyl-propan-1-ol [J. Med. Chem. 33, 2707 (1990)] in 200 ml of a 4N solution of gaseous hydrogen chloride in anhydrous dioxane is stirred at room temperature for 30 minutes. Thereafter, 60 ml of toluene are added and the mixture is concentrated in vacuo. This operation is repeated twice more, and the residue is then titrated with a little ether, filtered off with suction and dried under a high vacuum over KOH. 14.14 g (94% of theory) of the title compound are obtained as colourless crystals.

Melting point: 148°–150° C. (ether). $R_f$=0.25 (acetonitrile:water 9:1). MS (DCI, NH$_3$) m/z=152 (M+H)$^+$. IR (KBr) 3357, 2928, 1571, 1495, 1456, 1026, 738, 708 cm$^{-1}$. $[\alpha]_D^{20}$=–4.2° (c=2.94, CH$_3$OH). $^1$H-NMR (300 MHz, CD$_3$OD) δ=2.95 (d, 2H, J=7.5 Hz, CH$_2$); 3.50 (m, 2H); 3.70 (m, 1H); 7.30 (m, 5H, Ph). C$_9$H$_{13}$NO×HCl (187.67).

EXAMPLE II (2S)-2-[N-(tert-Butoxycarbonyl)-S-valinyl]
amino-3-phenyl-propan-1-ol

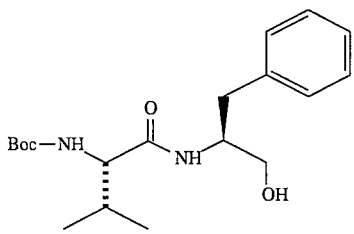

16.32 g (79.10 mmol) of DCC are added to a stirred solution, cooled to 0° C., of 18.01 g (82.90 mmol) of N-(tert-butoxycarbonyl)-L-valine and 12.69 g (82.90 mmol) of HOBT in 300 ml of anhydrous methylene chloride, and the mixture is stirred for 5 minutes. Thereafter, a solution of 14.14 g (75.40 mmol) of the compound from Example I and 20.73 g (188.50 mmol) of N-methylmorpholine in 300 ml of methylene chloride is added dropwise. The cooling bath is removed and the reaction mixture may be stirred at room temperature for 2 hours. The end of the reaction is determined by thin layer chromatography. The urea formed is removed by filtration, the filtrate is concentrated in vacuo and the crude product is purified by chromatography on 450 g of silica gel (methylene chloride: methanol 95:5). 25.15 g (95% of theory) of the title compound are obtained as colourless crystals.

Melting point: 143° C. $R_f$=0.29 (methylene chloride: methanol 95:5). MS (FAB) m/z=351 (M+H)$^+$. IR (KBr) 3340, 2933, 1686, 1657, 1523, 1368, 1311, 1246, 1172, 1044, 698 cm$^{-1}$. $[\alpha]_D^{20}$=42.1° (c=0.401, CH$_3$OH). $^1$H-NMR (300 MHz, CD$_3$OD) δ=0.87 (t, J=7 Hz, 6H [CH$_3$]$_2$CH); 1.44 (s, 9H, CH$_3$-C); 1.93 (m, 1H, [CH$_3$]$_2$ CH); 2.74 (dd, J=8, 14 Hz, 1H, CH$_2$Ph); 3.92 (dd, J=6 Hz, 14 Hz, 1 H CH$_2$Ph); 3.50 (d, J=6 Hz, 2H, CH$_2$OH); 3.79 (d, J=7 Hz, 1H, NCHCO); 4.12 (m, 1H, NCH); 7.23 (m, 5H, Ph) . C$_{19}$H$_{30}$N$_2$O$_4$ (350.47).

EXAMPLE III (2S)-2-(N-S-Valinyl)amino-3-phenyl-propan-1-ol

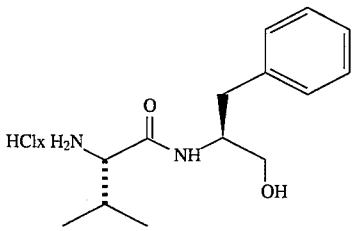

180 ml of a 4N solution of gaseous hydrogen chloride in anhydrous dioxane are added to a solution of 25.15 g (75.6 mmol) of the compound from Example I in 180 ml of anhydrous dioxane and the mixture is stirred at room temperature for 30 minutes. Thereafter, 150 ml of toluene are added and the mixture is concentrated in vacuo. This operation is repeated twice more, and the residue is then titrated with 300 ml of ether, filtered off with suction and dried under a high vacuum over KOH. 20.12 g (98% of theory) of the title compound are obtained as colourless crystals.

Melting point: above 100° C. (decomposition). $R_f$=0.19 (acetonitrile: water 9:1 ). MS (DCI, NH$_3$) m/z=251 (M+H)$^+$. IR (KBr) 3267, 2931, 1670, 1571, 1496, 1259, 1120, 1040, 870 cm$^{-1}$. $[\alpha]_D^{20}$=2.5° (c=0.375, CH$_3$OH). $^1$H-NMR (300 MHz, CDCl$_3$) δ=1.03, 1.07 (d, 7 Hz, 6H, [CH$_3$]$_2$CH); 2.20 (m, 1H, [CH$_3$]$_2$CH); 2.88 (AB, J=7.5, 15 Hz, 2H, CH$_2$Ph); 3.54 (m, 2H, CH$_2$OH); 3.63 (d, J=6.5 Hz, 1H, NCHCO); 4.16 (1H, NCH); 7.28 (m, 5H, Ph). C$_{14}$H$_{22}$N$_2$O$_2$×HCl (286.80). Calculated: C 58.63 H 8.08 N 9.77. Found: C 58.7 H 8.3 N 9.5.

EXAMPLE IV (2S)-2-[Nα-(tert-Butoxycarbonyl)-N$^G$-
(4-methyl-phenylsulphonyl)-S-arginyl-S-valinyl]
amino-3-phenyl-propan-1-ol

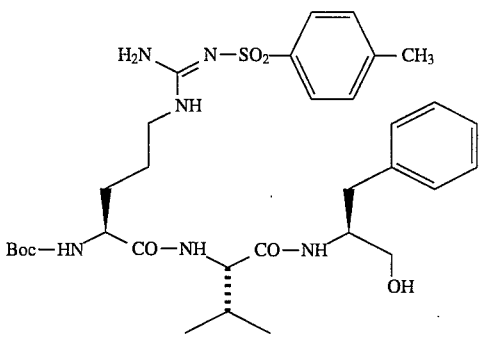

8.57 g (41.50 mmol) of DCC are added to a stirred solution, cooled to 0° C., of 18.64 g (43.51 mmol) of N$_\alpha$-(tert-butoxycarbonyl)-N$^G$-(4-methylphenylsulphonyl)-S-arginine and 6.66 g (43.50 retool) of HOBT in 190 ml of anhydrous methylene chloride and 19 ml of DMF, and the mixture is stirred for 5 minutes. Thereafter, a solution of 11.33 g (39.50 mmol) of the compound from Example III and 17.38 ml (158.10 mmol) of N-methylmorpholine in 113 ml of methylene chloride and 11 ml of DMF is added dropwise. The cooling bath is removed and the reaction mixture may be stirred at room temperature for 1 hour. The end of the reaction is determined by thin layer chromatography. The urea formed is removed by filtration, the filtrate is concentrated in vacuo and the crude product is purified by chromatography on 500 g of silica gel (methylene chloride:methanol 9:1). 18.98 g (73% of theory) of the title compound are obtained as a colourless foam.

$R_f$=0.35 (methylene chloride:methanol 9:1). MS (FAB) m/z=661 (M+H)$^+$. IR (KBr) 3336, 2967, 1654, 1544, 1253, 1168, 1131, 1082, 676 cm$^{-1}$. $[\alpha]_D^{20}$=−32.7° (c=0.895, CH$_3$OH). $^1$H-NMR (250 MHz, CD$_3$OD) δ=0.89 (m, 6H, [CH$_3$]$_2$CH); 1.43 (s, 9H, CH$_3$-C); 1.4–1.6 (m, 4H, CH$_2$); 1.99 (m, 1H, [CH$_3$]$_2$ CH); 2.38 (s, 3H, CH$_3$); 2.70 (dd, J=10, 16 Hz, 1H, CH$_2$Ph); 2.90 (dd, J=7.5, 15 Hz, 1H, CH$_2$Ph); 3.13 (m, 2H, CH$_2$N); 3.50 (d, J=7 Hz, 2H, CH$_2$O); 3.72 (m, 1H, NCHCO); 4.0–4.2 (m, 2H, NCHCO, NCH); 7.20 (m, 5H, Ph); 7.30, 7.73 (AB, J=10 Hz, 4H, H aromatic). C$_{32}$H$_{48}$N$_6$O$_7$S (660.85 ). Calculated: C 58.16 H 7.32 N 12.72. Found: C 58.3 H 7.4 N 12.6.

EXAMPLE V (2S)-2-[N$^G$-(4-Methyl-phenylsulphonyl)-S-arginyl-S-valinyl]amino-3-phenyl-propan-1-ol dihydrochloride

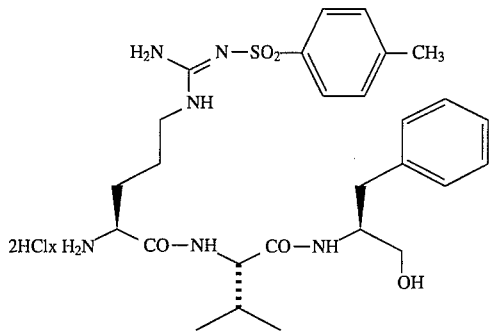

18.68 g (99% of theory) of the title compound are obtained as a colourless powder from 18.90 g (28.60 mmol) of the compound from Example IV as described for Example I.

Melting point: 161°–162° C. $R_f$=0.36 (acetonitrile:water 9:1). MS (FAB) m/z=561 (M+H)$^+$. IR (KBr) 2964, 1655, 1560, 1342, 1171, 1090, 1041, 666 cm$^{-1}$. [α]$_D^{20}$=2.3° (c=0.983, CH$_3$OH). $^1$H-NMR (250 MHz, DC$_3$OD) δ=0.96 (m, 6H, [CH$_3$]$_2$CH); 1.50 (m, 2H, CH$_2$); 1.80 (m, 2H, CH$_2$); 2.03 (m, 1H [CH$_3$]$_2$CH); 2.42 (s, 3H, CH$_3$); 2.68 (dd, J=8 Hz, 14 Hz, 1H, CH$_2$Ph); 2.86 (dd, J=6 Hz, 14 Hz, 1H, CH$_2$Ph); 3.12 (t, J=6.5 Hz, 2H, CH$_2$N); 3.51 (d, J=6 Hz, 2H, CH$_2$O); 3.97 (m, 1H, NCHCO-Arg); 4.07 (m, 1H, NCH); 4.18 (d, J=7.5 Hz, NCHCO-Val); 7.18 (m, 5H, Ph); 7.45, 7.87 (AB, J=10 Hz, 4 H, H aromatic). C$_{27}$H$_{40}$N$_6$O$_5$S×2 HCl (633.66). Calculated: C 51.18 H 6.68 N 13.26. Found: C 4 9.9 H 6.8 N 13.3.

EXAMPLE VI

Nα-(tert-Butoxycarbonyl)-N$^G$-(4-methyl-phenylsulphonyl)-S-arginyl-S-valinyl-S-phenylalanine methyl ester

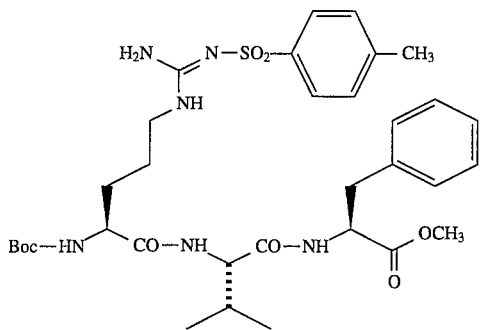

13.66 g (69% of theory) of the title compound are obtained as a colourless foam from 14.14 g (33.00 mmol) of N$_α$-(tert-butoxycarbonyl)-N$^G$-(4-methyl-phenylsulphonyl)-S-arginine and 9.02 g (28.70 mmol) of S-valinyl-S-phenylalanine methyl ester hydrochloride [EP 77 029; A. Orlowska et al. Pol. J. Chem. 54, 2329 (1980)] after 3 hours at room temperature, as described for Example IV.

$R_f$=0.33 (ethyl acetate). MS (FAB) m/z=689 (M+H)$^+$. IR (KBr) 3343, 2967, 1740, 1655, 1546, 1254, 1169, 1132, 1083, 676 cm$^{-1}$. [α]$_D^{20}$=−9.1° (c=0.389, DMSO). $^1$H-NMR (250 MHz, DMSO$_{d6}$/D$_2$O): δ=0.82 (m, 6H, [CH$_3$]$_2$CH); 1.49 (s, CH$_3$-C); 1.3–1.5 (m, CH$_2$)together 13H, 1.95 (m, 1H, [CH$_3$]$_2$ CH); 2.35 (s, 3H, CH$_3$); 3.05 (m, 4H, CH$_2$Ph, CH$_2$N); 3.60 (s, 3H, COOCH$_3$); 3.89 (m, 1H, NCHCO); 4.49 (m, 1H, NCHCO); 7.15–7.30 (m, 5H, Ph); 7.33, 7.68 (AB, J=10 Hz, 4H, H aromatic).

EXAMPLE VII

N$^G$-(4-Methyl-phenylsulphonyl)-S-arginyl-S-valinyl-S-phenylalanine methyl ester dihydrochloride

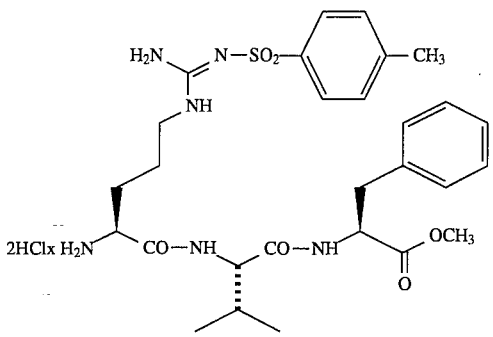

10.18 g (92% of theory) of the title compound are obtained as a colourless powder from 11.50 g (16.70 mmol) of the compound from Example VI as described for Example I.

Melting point: above 190° C. (decomposition). $R_f$=0.18 (methylene chloride:methanol 9:1). MS (FAB): m/z=589 (M+H)$^+$. IR (KBr) 2963, 1744, 1670, 1549, 1364, 1218, 1171, 1086, 668 cm$^{-1}$. [α]$_D^{20}$=7.6° (c=0.493, DMSO). $^1$H-NMR (250 MHz, DMSO$_{d6}$/CD$_3$OD) δ=0.97 (d, J=8 Hz, 6H, [CH$_3$]$_2$CH); 1.41, 1.62 (m, 4H, CH$_2$); 2.00 (m, 1H, [CH$_3$]$_2$ CH); 2.35 (s, 3H, CH$_3$ ); 2.90–3.15 (m, 4H, CH$_2$Ph, CH$_2$N); 3.58 (s, 3H, COOCH$_3$); 3.86 (m, 1H, NHCHCO); 4.25 (m, NCHCO, under HDO); 4.52 (m, 1H, NCHCO); 7.22 (m, 5H, Ph); 7.30, 7.68 (AB, J=9 Hz, 4H, H aromatic).

EXAMPLE VIII AND EXAMPLE IX (2S)-2-{N$_α$-[((1S)-1-Carboxy-2-phenyl-ethyl)aminocarbonyl]-S-arginyl-S-valinyl}amino-3-phenyl-propan-1-al (=α-MAPI).

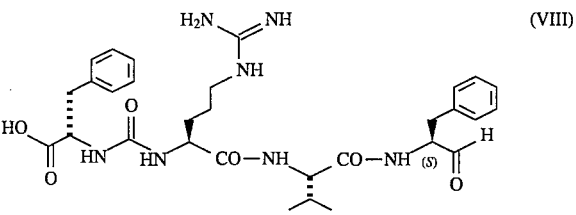

and (2R)-2-{N$_\alpha$-[((1S)-1-Carboxy-2-phenyl-ethyl)
aminocarbonyl]-S-arginyl-S-valinyl}
amino-3-phenyl-propan-1-al (=β-MAPI)

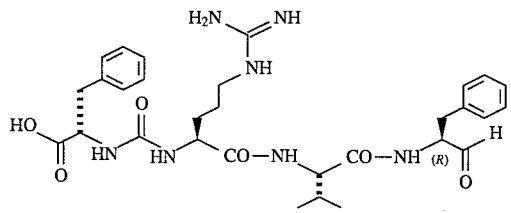

3.59 g (22.6 mmol) of pyridine/sulphur trioxide complex are added to a solution of 3.00 g (5.02 mmol) of the compound from Example 3 in 45 ml of DMSO and 6.3 ml (45.20 mmol) of triethylamine, and the mixture is stirred at room temperature for 1 hour. Thereafter, the reaction mixture is stirred into 400 ml of ether, an oil separating out. The ether phase is decanted off and the oil which remains is chromatographed over 500 g of silica gel (chloroform-:methanol:water:acetic acid=13:3:1:1). The fractions containing product are collected, 100 ml of toluene are added and the mixture is concentrated in vacuo. The residue is taken up in 50 ml of toluene and the toluene is evaporated off in vacuo. The residue is titrated with 80 ml of anhydrous acetonitrile, a crystalline precipitate forming. This is separated off by filtration, washed with 10 ml of acetonitrile, titrated with 2×10 ml of ether, filtered off with suction and dried under a high vacuum. 850 mg (28%) of the title compound are obtained as a mixture of the diastereomeric aldehydes (α,β-MAPI).

Melting point: 214° C. (decomposition). $R_f$=0.29 (chloroform:methanol:water:acetic acid 13:3:1:1).

To separate the diastereomeric aldehydes, 150 mg of the mixture are dissolved in 1 ml of formic acid and the mixture is chromatographed on an HPLC unit (column: Dynamax®-60 A, 21.4×250 mm, Rainin Instrument Company No. 83-221-C; type: C18, particle size: 8 µm; pore size: 60 A, flow rate: 10 ml/minute; eluent:water:methanol 1:1+0.05% of trifluoroacetic acid). The fractions containing product are collected and freeze dried. 56 mg of the (2S)-isomer (α-MAPI) (VIII).

MS(FAB) m/z=596 (M+H)$^+$, 749 (M+NBA+H)$^+$. IR (KBr): 3380, 2990, 2930, 1640, 1546, 1203, 700 cm$^{-1}$ 37 mg of a mixed fraction (α,β-MAPI) (VIII+IX) and 39 mg of the (2R)-isomer (β-MAPI) (IX).

MS (FAB) m/z=596 (M+H)$^+$, 749 (M+NBA+H)$^+$. IR (KBr) 3407, 2998, 2935, 1654, 1560, 1204, 701 cm$^{-1}$ are obtained.

The $^1$H-NMR spectroscopic data are identical to the diastereomeric aldehydes obtained from *Streptomyces nigrescens* WT-27:

(4) α-MAPI: (T. Watanabe, K. Fukuhara, S. Murao, Tetrahedron Lett. 625 (1979).

(5) β-MAPI: (T. Watanabe, K. Fukuhara, S. Murao, Tetrahedron 38, 1775 (1982).

EXAMPLE X

N$_\alpha$-[((1S)-1-Carboxy-2-phenyl-ethyl)aminocarbonyl]-
S-arginyl-S-valinyl-S-phenylalanine

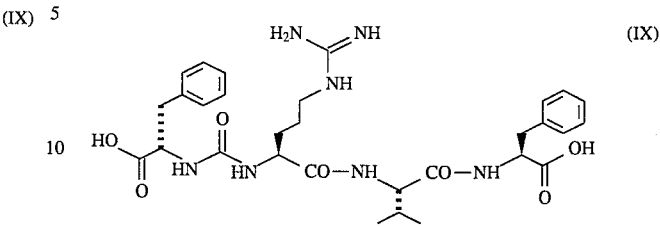

221 mg (70%) of the title compound are obtained as a colourless powder from 330 mg (0.52 mmol) of the compound from Example 8 and 96 mg (2.26 mmol) of lithium hydroxide hydrate in a mixture of 2 ml of THF and 2.2 ml of water as described for Example 2.

Melting point: above 217° C. (decomposition). $R_f$=0.29 (chloroform:methanol 7:3). MS (FAB) m/z=612 (M+H)$^+$. IR (KBr) 3310, 1639, 1543, 1390, 1219, 701 cm$^{-1}$. $[\alpha]_D^{20}$= 31.6° (c=0.0558, DMSO). $^1$H-NMR (250 MHz, DMSO$_{d6}$/D$_2$O) δ=0.72, 0.80 (d, J =6.5 Hz, 6H, [CH$_3$]$_2$CH); 1.40–1.80 (m, 4H, CH$_2$); 1.92 (m, 1H, [CH$_3$]$_2$CH); 2.80–3.10 (m, 6H, CH$_2$Ph, CH$_2$N); 3.91 (d, J=6.5 Hz, 1H, NCHCO-valine); 4.14 (m, 1H, NCHCO); 4.23 (m, 2H, NCHCO); 7.10–7.30 (m, 10H, Ph).

PREPARATION EXAMPLES

EXAMPLE 1

(2S )-2-{N$_\alpha$-[((1S)
-1-Methoxycarbonyl-2-phenyl-ethyl)aminocarbonyl]-
N$^G$-(4 -methoxy-phenylsulphonyl)-S-arginyl-
S-valinyl}amino-3-phenyl-propan-1-ol

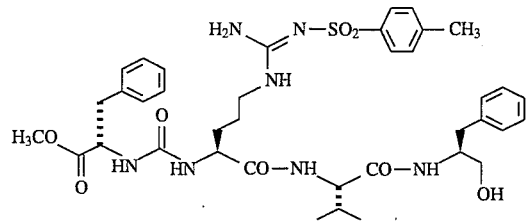

1.01 ml (7.26 mmol ) of triethylamine are added to a stirred suspension of 2.00 g (3.16 mmol) of the compound from Example V in 60 ml of anhydrous methylene chloride, a clear solution being formed. 712 mg (3.47 mmol ) of (2S)-methyl 2-isocyanato-3-phenyl-propanoate [U.S. Pat. No. 4,929,736; H. Danda et al., Chem. Express 6, 261 (1991)] are added thereto and the mixture is subsequently stirred at room temperature for 30 minutes. 40 ml of toluene are added, the reaction mixture is concentrated in vacuo and the residue is purified by chromatography over 220 g of silica gel (methylene chloride:methanol 92:8). 2.12 g (88%) of the title compound are obtained as colourless crystals.

Melting point: 153° C. $R_f$=0.33 (methylene chloride:methanol 9:1). MS (FAB) m/z=766 (M+H)$^+$. IR (KBr) 3342, 2980, 1742, 1624, 1550, 1269, 1133, 1082, 674 cm$^{-1}$. $[\alpha]_D^{20}$=–9.0° (c=0.85, DMSO). $^1$H-NMR (250 MHz, DMSO$_{d6}$/D$_2$O): δ=0.78 (m, 6H, [CH$_3$]$_2$CH); 1.30–1.55 (m, 4H, CH$_2$); 1.88 (m, 1H, [CH$_3$]$_2$CH); 2.35 (s, 3H, CH$_3$); 2.60 (dd, J=9 Hz, 14 Hz, 1H, CH$_2$Ph); 2.86 (dd, J=6 Hz, 14 Hz, 1H, CH$_2$Ph); 2.92–3.10 (m, 4H, CH$_2$Ph, CH$_2$N); 3.32 (m, 2H, CH$_2$O); 3.59 (s, 3H, COOCH$_3$); 3.90–4.10 (m, 3H, NCHCO, NCH); 4.40 (m, 1H, NCHCO); 7.13–7.33 (m, 12H, H aromatic); 7.65 (d, J=10 Hz, H aromatic). C$_{38}$H$_{51}$N$_7$O$_8$S (765.95). Calculated: C 59.59 H 6.71 N 12.80. Found: C 59.3 H 6.7 N 12.8.

EXAMPLE 2

(2S )-2-{N$_{60}$ -[((1S)
-1-Carboxy-2-phenyl-ethyl)aminocarbonyl]-N$^G$-(4
-methyl-phenylsulphonyl)-S-arginyl-S-valinyl}
amino-3-phenyl-propan-1-ol

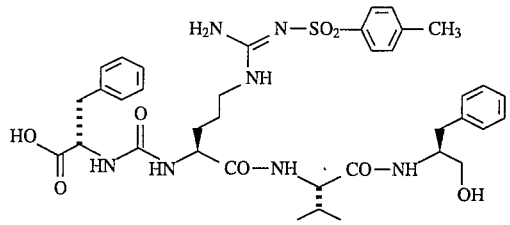

544 mg (12.96 mmol) of lithium hydroxide hydrate are added to a solution of 4.96 g (6.48 mmol) of the compound from Example 1 in 16 ml of THF and 20 ml of water, and the mixture is stirred at room temperature for 20 minutes. Thereafter, the reaction mixture is shaken in 100 ml of ethyl acetate. The organic phase is separated off and the aqueous phase is extracted again with 30 ml of ethyl acetate. The aqueous phase is freed from residues of solvent on a rotary evaporator and brought to pH 5.2 with 0.5N hydrochloric acid. The precipitate formed is stirred thoroughly for 10 minutes, separated off by filtration and dried under a high vacuum first over KOH and then over Sicapent. 4.14 g (85%) of the title compound are obtained as a colourless powder.

Melting point: above 140° C. (decomposition). R$_f$=0.21 (acetonitrile:water 9:1). MS (FAB): m/z=732 (M+H)$^+$, 774 (M+Na)$^+$. IR (KBr) 3346, 2962, 1730, 1637, 1549, 1253, 1132, 1082, 700 cm$^{-1}$. [α]$_D^{20}$=–5.5° (c=0.704, DMSO). $^1$H-NMR (300 MHz, DMSO-d$_6$, D$_2$O): δ=0.75 (m, 6H, [CH$_3$]$_2$CH); 1.30–1.60 (m, 4H, CH$_2$); 1.90 (m, 1H, [CH$_3$]$_2$CH); 2.35 (s, 3H, CH$_3$); 2.61 (dd, J=7 Hz, 13 Hz, 1H, CH$_2$Ph); 2.80–3.10 (m, 5H, CH$_2$Ph, CH$_2$N); 3.31 (m, 2H, CH$_2$O); about 4.0 under HDO: (NCHO, NCH); 4.38 (m, 1H, NCHCO); 7.10–7.30 (m, 12H, H aromatic); 7.67 (d, J=10 Hz, 2H, H aromatic). C$_{37}$H$_{49}$N$_7$O$_8$S (751.91). Calculated: C 59.10 H 6.57 N 13.04. Found: C 60.1 H 6.7 N 12.8.

EXAMPLE 3

(2S)-2-{N$_\alpha$-[((1S)-1-Carboxy-2-phenyl-ethyl)
aminocarbonyl]-S-arginyl-S-valinyl}
amino-3-phenyl-propan-1-ol hydrofluoride

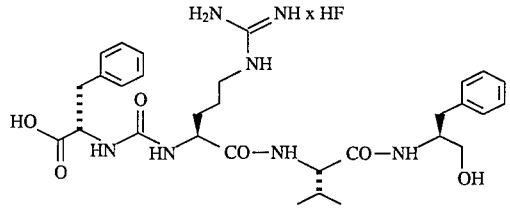

A solution of 2.00 g (2.66 mmol) of the compound from Example 2 and 1.00 g (9.25 mmol) of p-cresol in 20 ml of anhydrous hydrofluoric acid is stirred at 0° C. for 20 minutes. The hydrofluoric acid is then stripped off in vacuo, the residue is dissolved in 60 ml of acetic acid and the solution is stirred into a mixture of 200 ml of ethyl acetate and 600 ml of water. The aqueous phase is separated off and freeze dried. 1.48 g (94%) of the title compound are obtained as a colourless lyophilisate.

R$_f$=0.27 (acetonitrile:water 4:1). MS (FAB) m/z=598 (M+H)$^+$. IR (KBr) 3380, 1655, 1637, 1560, 1204, 700 cm$^{-1}$. [α]$_D^{20}$=–4.9° (c=0.635, DMSO). $^1$H-NMR (250 MHz, DMSO-d$_6$, D$_2$O): δ=0.78 (s, 6H, [CH$_3$]$_2$CH); 1.45–1.65 (m, 4H, CH$_2$); 1.90 (m, 1H, [CH$_3$]$_2$CH); 2.61 (dd, 9.4 Hz, 15 Hz, 1H, CH$_2$Ph); 2.80–3.10 (m, 5H, CH$_2$Ph, CH$_2$N); 3.85 (m, 2H, CH$_2$O); 3.95–4.15 under HDO (NCHCO, NCH); 4.48 (m, 1H, NCHCO); 7.15–7.35 (m, 10H, H aromatic).

EXAMPLE 4 AND EXAMPLE 5

(2R)-2-{N$_\alpha$-[(1S)-1-Methoxycarbonyl-2-phenyl-ethyl)
aminocarbonyl]-N$^G$-(4
-methyl-phenylsulphonyl)-S-arginyl-S-valinyl}amino-
3-phenyl-propan-1-al

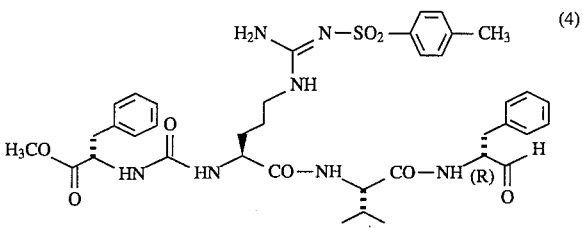

and (2S)-2-{N$_\alpha$-[((1S)-1-Methoxycarbonyl-2-phenyl-ethyl)
aminocarbonyl]-N$^G$-(4
-methyl-phenylsulphonyl)-S-arginyl-S-valinyl}
amino-3-phenyl-propan-1-al

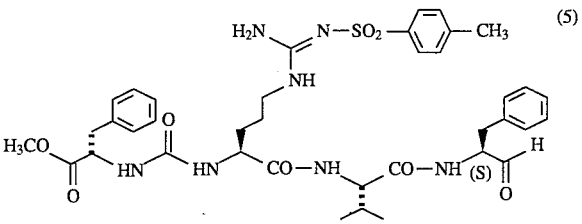

468 mg (2.94 mmol) of pyridine/sulphur trioxide complex are added to a solution of 500 mg (0.65 mmol) of the compound from Example 1 in 4.8 ml of DMSO and 0.82 ml (5.87 mmol) of triethylamine, and the mixture is stirred at room temperature for 30 minutes. Thereafter, the reaction mixture is stirred into 50 ml of ether. The mixture is allowed to stand for a short time, an oil separating out. The ether phase is decanted off and the oil is taken up in 20 ml of toluene. The toluene is evaporated in vacuo and the residue is chromatographed over 250 g of silica gel (methylene chloride:methanol 9:1).

179 mg (36%) of the non-polar diastereomer (4) are obtained as colourless crystals.

Melting point: 126° C. (decomposition). R$_f$=0.39 (methylene chloride:methanol 9:1). MS (FAB) m/z=764 (M+H)$^+$. IR (KBr) 3346, 2959, 1736, 1637, 1550, 1256, 1132, 1082, 700 cm$^{-1}$. [α]$_D^{20}$=26.4° (c=0.489, DMSO). $^1$H-NMR (250 MHz, DMSO-d$_6$): δ=0.65 (t, J=7 Hz, 6H, [CH$_3$]$_2$CH); 1.3–1.6 (m, 4H, CH$_2$); 1.80 (m, 1H, [CH$_3$]$_2$ CH); 2.32 (s, 3H, CH$_3$); 2.65–3.10 (m, 6H, CH$_2$Ph, CH$_2$N); 3.58 (s, 3H, COOCH₃); 4.12 (m, 2H, NCHCO); 4.38 (m, 2H, NCHCO); 6.43 (d, J=9 Hz, 1H, NH); 7.10–7.30 (m, 12H, H aromatic); 7.62 (d, J=8 Hz, 2H, H aromatic); 7.28 (d, J=9 Hz, 1H, NH); 8.46 (d, J=7.5 Hz, 1H, NH); 9.48 (s, 1H, CHO).

168 mg (30%) of the polar diastereomer (5) are furthermore obtained as colourless crystals.

Melting point: 156° C. (decomposition). $R_f$=0.35 (methylene chloride:methanol 9:1). MS (FAB) m/z=764 (M+H)⁺. IR (KBr) 3357, 2964, 1736, 1625, 1550, 1275, 1133, 1082, 672 cm⁻¹. $[\alpha]_D^{20}$=−7.9° (c=0.538, DMSO). ¹H-NMR (250 MHz, DMSO-d₆): δ=0.78 (m, 6H, [CH₃]₂CH); 1.20–1.60 (m, 4H, CH₂); 1.89 (m, 1H, [CH₃]₂CH); 2.32 (s, 3H, CH₃); 2.70–3.10 (m, 6H, CH₂Ph, CH₂N); 3.57 (s, 3H, COOCH₃); 4.10 (m, 2H, NCHCO); 4.38 (m, 2H, NCHCO); 6.40 (d, J=8 Hz, 1H, NH); 7.10–7.30 (m, 12H, H aromatic); 7.62 (d, J=8 Hz, 2H, H aromatic); 7.29 (d, J=9 Hz, 1H, NH); 8.42 (d, J=6.5 Hz, 1H, NH); 9.42 (s, 1H, CHO).

EXAMPLE 6

$N_{60}$-[((1S)-1-Methoxycarbonyl-2-phenyl-ethyl) aminocarbonyl]-$N^G$-(4 -methyl-phenylsulphonyl)-S-arginyl-S-valinyl-S-phenylalanine methyl ester

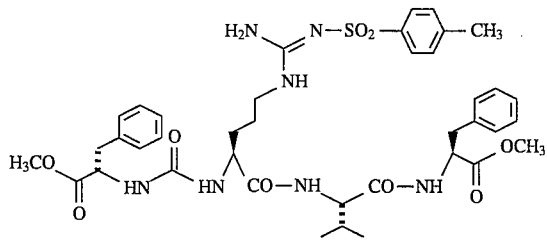

9.75 g (85%) of the title compound are obtained as colourless crystals from 9.85 g (14.90 mmol) of the compound from Example VII and 3.67 g (17.88 mmol) of (2S)-methyl 2-isocyanato-3-phenyl-propanoate [U.S. Pat. No. 4,929,736] as described for Example 1.

Melting point: 200°–201° C. $R_f$=0.44 (methylene chloride:methanol 9:1). MS (FAB) m/z=794 (M+H)⁺. IR (KBr) 3316, 2968, 1748, 1626, 1551, 1276, 1213, 1136, 1084, 700, 672 cm⁻¹. $[\alpha]_D^{20}$=−2.0° (c=0.58, DMSO). ¹H-NMR (200 MHz, DMSO-d₆) δ=0.78 (t, J=5.5 Hz, 6H, [CH₃]₂CH); 1.20–1.55 (m, 4H, CH₂); 2.32 (s, 3H, CH₃); 2.80–3.10 (m, 4H, CH₂Ph, CH₂ N); 3.55 (s, 3H, COOCH₃); 3.59 (s, 3H, COOCH₃); 4.18 (m, 2H, NCHCO); 4.31–4.52 (m, 2H, NCHCO); 6.41 (d, J=7.5 Hz, 1H, NH); 7.10–7.30 (m, 7H, H aromatic); 7.63 (d, J=9 Hz, 2H, H aromatic); 7.78 (d, J=9.5 Hz, NH); 8.42 (d, J=7 Hz, NH). C₃₉H₅₁N₇O₉S (793.95). Calculated: C 59.00 H 6.47 N 12.35. Found: C 58.9 H 6.5 N 12.3.

EXAMPLE 7

$N_{60}$-[((1S)-1-Carboxy-2-phenyl-ethyl)aminocarbonyl]-$N^G$-(4 -methyl-phenylsulphonyl)-S-arginyl-S-valinyl-S-phenylalanine

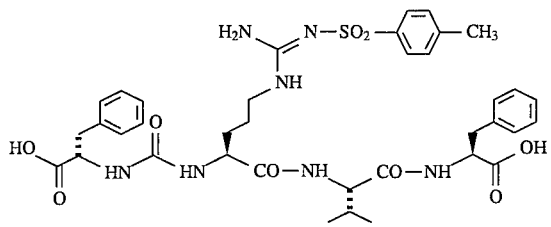

380 mg (78%) of the title compound are obtained as a colourless powder from 500 mg (0.63 mmol) of the compound from Example 6 and 106 mg (2.52 mmol) of lithium hydroxide hydrate in a mixture of 3.5 ml of THF and 4 ml of water as described for Example 2.

Melting point: above 143° C. (decomposition). $R_f$=0.26 (acetonitrile:water 85:15). MS (FAB) m/z=766 (M+H)⁺, 772 (M+Li)⁺. IR (KBr) 3356, 2965, 1743, 1638, 1550, 1400, 1252, 1131, 1081, 700 cm⁻¹. $[\alpha]_D^{20}$=10.5° (c=0.633, DMSO). ¹H-NMR (250 MHz, DMSO-d₆/D₂O) δ=0.78 (m, 6H, [CH₃]₂CH); 1.15–1.60 m (4H, CH₂); 1.93 (m, 1H, [CH₃]₂CH); 2.34 (s, 3H, CH₃); 2.80–3.10 (m, 6H, CH₂Ph, CH₂N); 4.11 (m, 2H, NCHCO); 4.30–4.45 (m, 2H, NCHCO); 7.20 (m, 12H, H aromatic); 7.65 (d, J=8 Hz, 2H, H aromatic).

EXAMPLE 8

$N_\alpha$-[((1S)-1-Methoxycarbonyl-2-phenyl-ethyl) aminocarbonyl]-S-arginyl-S-valinyl-S-phenylalanine methyl ester hydrofluoride

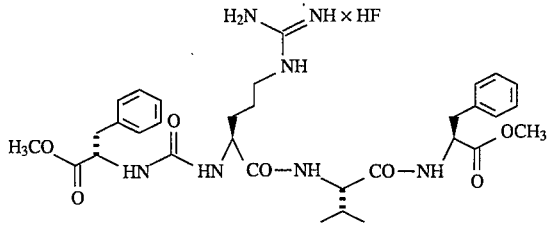

788 mg (79%) of the title compound are obtained as a colourless lyophilizate of pH 5.8 from 1.20 g (1.51 mmol) of the compound from Example 6 in the presence of 1.20 g (11.10 mmol) of p-cresol and 12 ml of anhydrous hydrofluoric acid, after chromatography of the crude product over 20 g of silica gel (acetonitrile:water 4:1), as described for Example 3.

$R_f$=0.30 (acetonitrile:water 4:1). MS (FAB) m/z=640 (M+H)⁺. IR (KBr) 3357, 1741, 1638, 1560, 1216, 700 cm⁻¹. ¹H-NMR (250 MHz, DMSO-d₆/D₂O) δ=0.82 (m, 6H, [CH₃]₂CH); 1.35–1.60 (m, 4H, CH₂); 1.95 (m, 1H, [CH₃]₂CH); 2.60–3.10 (m, 6H, CH₂Ph, CH₂N); 3.59 (s, 3H, COOCH₃); 3.62 (s, 3H, COOCH₃); 4.10 (m, 2H, NCHCO); 4.40 (m, 1H, NCHCO); 4.50 (m, 1H, NCHCO); 7.12–7.35 (m, 10H, H aromatic).

EXAMPLE 9

(2S)-2-{$N_\alpha$-[((2S)-1-Hydroxy-3-phenyl-prop-2-yl)aminocarbonyl]-$N^G$-(4-methyl-phenylsulphonyl)-S-arginyl-S-valinyl}-amino-3-phenyl-propan-1-ol

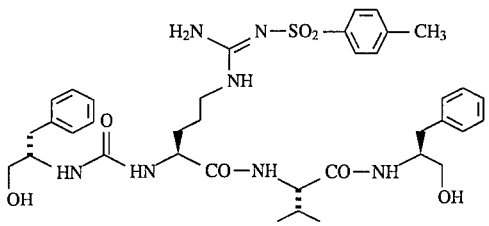

3.97 g (5.00 mmol) of the compound from Example 6 are added in portions to a stirred solution, heated to 40° C., of 454 mg (12.00 mmol) of sodium borohydride and 1.61 g (12.00 mmol) of lithium iodide in 30 ml of THF in the course of 10 minutes. 8 ml of methanol are slowly added dropwise to this mixture at 40° C. in the course of 5 hours. The end of the reaction is determined by thin layer chromatography and the reaction mixture is shaken in 60 ml of a 10% strength solution of citric acid. This mixture is extracted with 4×30 ml of ethyl acetate and the combined extracts are dried over $MgSO_4$. After the solvent has been evaporated off in vacuo and the residue has been chromatographed over 208 g of silica gel (methylene chloride:methanol 9:1), 2.11 g (57%) of the title compound are obtained as colourless crystals.

Melting point: 114° C. $R_f$=0.31 (methylene chloride:methanol 85:15). MS (FAB): m/z=738 (M+H)$^+$. IR (KBr) 3340, 2932, 1642, 1550, 1255, 1132, 1081, 1041, 701, 676 cm$^{-1}$. $^1$H-NMR (250 MHz, DMSO$_{D6}$/CD$_3$OD) δ=0.78 (m, 6H, [CH$_3$]$_2$CH); 1.25–1.60 (m, 4H, CH$_2$); 1.93 (m, 1H, [CH$_3$]$_2$CH); 2.35 (s, 3H, CH$_3$); 2.60–2.90 (m, 4H, CH$_2$Ph); 3.08 (m, 2H, CH$_2$N); 3.32 (m, 4H, CH$_2$O); 3.76 (m, 1H, NCHCO); 3.97 (m, 1H, NCHCO); 4.10 (m, NCHCO under CD$_3$OD); 7.10–7.35 (m, 12H, H aromatic); 7.68 (d, J=9 Hz, 2H, H aromatic).

EXAMPLE 10

(2S)-2-{$N_\alpha$-[((2S)-1-Hydroxy-3-phenyl-prop-2-yl)aminocarbonyl]-S-arginyl-S-valinyl}amino-3-phenyl-propan-1-ol hydrofluoride

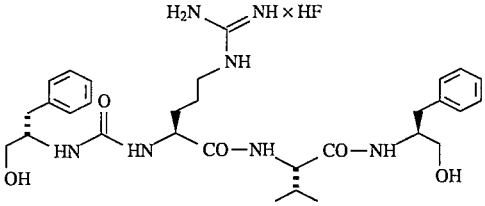

340 mg (61%) of the title compound are obtained as a colourless amorphous powder from 705 mg (0.96 mmol) of the compound from Example 9 in the presence of 705 mg (6.52 mmol) of p-cresol and 10 ml of anhydrous hydrofluoric acid, after chromatography of the crude product over 16 g of silica gel (acetonitrile:water 7:3), as described for Example 3.

$R_f$=0.14 (acetonitrile:water 4:1). MS (FAB): m/z=584 (M+H)$^+$. IR (KBr) 3407, 1638, 1560, 700 cm$^{-1}$. $[\alpha]_D^{20}$=−34.5° (c=0.503, DMSO). $^1$H-NMR (250 Hz, DMSO$_{d6}$/D$_2$O): δ=0.76 (m, 6H, [CH$_3$]$_2$CH); 1.30–1.65 (m, 4H, CH$_2$); 1.90 (m, 1H, [CH$_3$]$_2$CH); 2.62 (m, 2H, CH$_2$Ph); 2.82 (m, 2H, CH$_2$Ph); 3.10 (m, 2H, CH$_2$N); 3.33 (m, 4H, CH$_2$O); 3.76 (m, 1H, NCHCO); 3.92 (m, 1H under HDO, NCHCO); 4.02 (d, J=6.3 Hz, 1H, NCHCO-valine); 4.12 (m, 1H, NCHCO); 7.20 (m, 10H, H aromatic).

EXAMPLE 11

(2S)-2-{$N_\alpha$-[((1S)-1-Methoxycarbonyl-2-phenyl-ethyl)aminocarbonyl]-S-arginyl-S-valinyl}amino-3-phenyl-propan-1-ol hydrofluoride

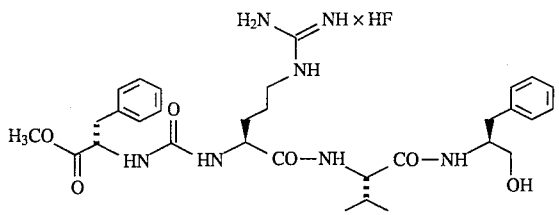

882 mg (82%) of the title compound are obtained as a colourless lyophilizate from 1.30 g (1.70 mmol) of the compound from Example 1 in the presence of 0.70 g of p-cresol and 13 ml of anhydrous hydrofluoric acid as described for Example 3.

$R_f$=0.49 (acetonitrile:water 4:1). MS (FAB) m/z=612 (M+H)$^+$. IR (KBr) 3422, 1736, 1654, 1560, 1216, 746 cm$^{-1}$. $[\alpha]_D^{20}$=−55.2° (c=0.6, DMSO). $^1$H-NMR (300 MHz, DMSO$_{d6}$/D$_2$O): δ=0.68 (m, 6H, [CH$_3$]$_2$CH); 1.40–1.85 (m, 5H, CH$_2$, [CH$_3$]$_2$CH); 2.53 (m, 1H, under DMSO, CH$_2$Ph); 2.80 (m, 3H, CH$_2$Ph); 2.98 (m, 2H, CH$_2$N); 3.16 (s, 3H, CO$_2$CH$_3$); 3.30 (m, 2H, CH$_2$O); 3.85 (m, 2H, NCHCO); 4.41 (m, 1H, NCHCO); 7.05–7.30 (m, 10H, H aromatic).

EXAMPLE 12

(2R,S)-2-{$N_\alpha$-[((1S)-1-Methoxycarbonyl-2-phenyl-ethyl)aminocarbonyl]-S-arginyl-S-valinyl}-amino-3-phenyl-propan-1-al

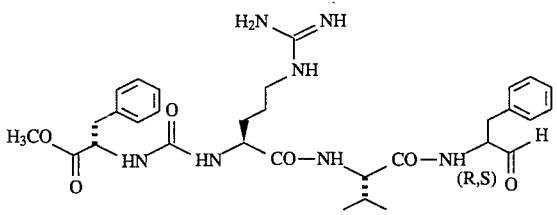

89 mg (47%) of the title compound are obtained as a colourless powder (mixture of the diastereomeric aldehydes) from 189 mg (0.31 mmol) of the compound from Example 11 and 221 mg (1.39 mmol) of pyridine/sulphur trioxide complex, after 1 hour at room temperature and chromatography of the crude product over 45 g of silica gel (chloroform:methanol:water:acetic acid 13:3:1:1), as described for Example 4 and Example 5.

Melting point: above 157° C. (decomposition). $R_f$=0.50 (acetonitrile:water 4:1). MS (FAB) m/z=610 (M+H)$^+$. IR (KBr) 3388, 1736, 1638, 1580, 700 cm$^{-1}$. $^1$H-NMR (250 MHz, DMSO-d$_6$, D$_2$O) δ=0.80 (m, 6H, [CH$_3$]$_2$CH]; 1.35–1.60 (m, 4H, CH$_2$); 1.92 (m, 1H, [CH$_3$]$_2$CH]; 2.7–3.2 (m, 6H, CH$_2$Ph, CH$_2$N); 4.20 (m, 2H, NCHCO); 4.38 (m, 2H, NCHCO); 7.1–7.3 (m, 10H, H aromatic); 9.45 (s, 1H, CHO).

EXAMPLE 13

(2R,S)-2-{N$_\alpha$-[((1S)-1-Carboxy-2-phenyl-ethyl)aminocarbonyl]-N$^G$-(4-methyl-phenylsulphonyl)-S-arginyl-S-valinyl}-amino-3-phenyl-propan-1-al

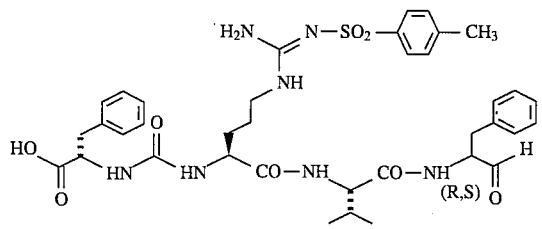

254 mg (85%) of the title compound are obtained as colourless crystals (mixture of the diastereomeric aldehydes) from 300 mg (0.40 mmol) of the compound from Example 2 and 286 mg (1.80 mmol) of pyridine/sulphur trioxide complex, after 1 hour at room temperature and chromatography of the crude product over 40 g of silica gel (methylene chloride:methanol 75:25), as described for Example 4.

Melting point: above 145° C. (decomposition). R$_f$=0.33 (methylene chloride:methanol 7:3). MS (FAB) m/z=750 (M+H)$^+$. IR (KBr) 3423, 1740, 1638, 1550, 1406, 1253, 1132, 1024, 700 cm$^{-1}$. $^1$H-NMR (200 MHz, DMSO-d$_6$/D$_2$O): δ=0.50–0.76 (m, 6H, [CH$_3$]$_2$CH); 1.25–1.60 (m, 4H, CH$_2$); 1.90 (m, 1H, [CH$_3$]$_2$ CH); 2.35 (s, 3H, CH$_3$); 2.80–3.10 (m, 6H, CH$_2$Ph, CH$_2$N); 4.10 (m, 2H, NCHCO); 4.41 (m, 1H, NCHCO); 4.77 (m, 1H, NCHCO); 7.20 (m, 10H, H aromatic); 7.30, 7.64 (AB, J=8.5 Hz, 4H, H aromatic); 9.61, 9.64 (s, 1H, CHO).

The products listed in Table 1 are obtained from the compound of Example V and the corresponding isocyanates (R$^1$=NCO) as described in Example 1:

TABLE 1

| Ex. No. | R$^2$ | R$^4$ | Yield (% of theory) | MS (FAB) m/z (M + H)$^+$ | R$_f$/mobile phase ratio | Melting point: (°C.) |
|---|---|---|---|---|---|---|
| 14 | -4-SO$_2$—C$_6$H$_4$—CH$_3$ | —CH$_2$—COOC$_2$H$_5$ | 67 | 690 | 0.25, I(9:1) | 195 |
| 15 | -4-SO$_2$—C$_6$H$_4$—CH$_3$ | —CH$_2$CH$_2$COOCH(CH$_3$)$_2$ | 95 | 718 | 0.17, I(9:1) | 229 |
| 16 | -4-SO$_2$—C$_6$H$_4$—CH$_3$ | —(CH$_2$)$_3$COOCH$_3$ | 73 | 704 | 0.25, I(9:1) | 159 |
| 17 | -4-SO$_2$—C$_6$H$_4$—CH$_3$ | —(CH$_2$)$_2$COO—nC$_4$H$_9$ | 76 | 732 | 0.23, I(9:1) | 120 |
| 18 | -4-SO$_2$—C$_6$H$_4$—CH$_3$ | —(CH$_2$)$_{11}$CH$_3$ | 72 | 772 | 0.21, I(9:1) | 151 |
| 19 | -4-SO$_2$—C$_6$H$_4$—CH$_3$ | -4-C$_6$H$_4$—COOC$_2$H$_5$ | 64 | 752 | 0.18, I(9:1) | 136 |
| 20 | -4-SO$_2$—C$_6$H$_4$—CH$_3$ | -4-C$_6$H$_4$—COCH$_3$ | 78 | 722 | 0.16, I(9:1) | 132 |
| 21 | -4-SO$_2$—C$_6$H$_4$—CH$_3$ | -4-C$_6$H$_4$—CF$_3$ | 76 | 748 | 0.20, I(9:1) | 174 |
| 22 | -4-SO$_2$—C$_6$H$_4$—CH$_3$ | -2-C$_6$H$_4$—COOC$_2$H$_5$ | 59 | 752 | 0.26, I(9:1) | 105 |
| 23 | -4-SO$_2$—C$_6$H$_4$—CH$_3$ | -4-C$_6$H$_4$—CH═CH—COOC$_2$H$_5$ | 77 | 778 | 0.39, I(9:1) | 142 |
| 24 | -4-SO$_2$—C$_6$H$_4$—CH$_3$ | [2,5-disubstituted phenyl with COOCH$_3$ groups] | 72 | 796 | 0.35, I(9:1) | 136 |
| 25 | -4-SO$_2$—C$_6$H$_4$—CH$_3$ | 3-C$_6$H$_4$—COOCH$_2$CH(CH$_3$)$_2$ | 83 | 780 | 0.29, I(9:1) | 115 |
| 26 | -4-SO$_2$—C$_6$H$_4$—CH$_3$ | 3-C$_6$H$_4$—COO(CH$_2$)$_3$CH$_3$ | 89 | 780 | 0.37, I(9:1) | 114 |
| 27 | -4-SO$_2$—C$_6$H$_4$—CH$_3$ | 4-C$_6$H$_4$—COO(CH$_2$)$_3$CH$_3$ | 87 | 780 | 0.36, I(9:1) | 128 |
| 28 | -4-SO$_2$—C$_6$H$_4$—CH$_3$ | 3-C$_6$H$_4$—COOC$_2$H$_5$ | 62 | 752 | 0.23, I(9:1) | 112 |
| 29 | -4-SO$_2$—C$_6$H$_4$—CH$_3$ | 3-C$_6$H$_4$—COOCH(CH$_3$)$_2$ | 56 | 766 | 0.44, I(9:1) | 145 |
| 30 | -4-SO$_2$—C$_6$H$_4$—CH$_3$ | —C(CH$_3$)$_3$ | 59 | 660 | 0.43, I(9:1) | 130 |
| 31 | [trimethylphenyl-SO$_2$- with O substituent] | —(CH$_2$)$_2$COOCH(CH$_3$)$_2$ | 56 | 830 | 0.51, I(9:1) | 198 |

TABLE 1-continued

[Structure: R₄—NH—C(=O)—NH—CH(side chain with guanidine N-R₂)—C(=O)—NH—CH(isopropyl)—C(=O)—NH—CH(CH₂-phenyl)—CH₂OH]

| Ex. No. | $R^2$ | $R^4$ | Yield (% of theory) | MS (FAB) m/z (M + H)⁺ | $R_f$/mobile phase ratio | Melting point: (°C.) |
|---|---|---|---|---|---|---|
| 32 | —SO₂—(2,3,5,6-tetramethylphenyl with O-tBu substituent) | -4-C₆H₄—COOC₂H₅ | 52 | 864 | 0.61, I(87:13) | 214 |
| 33 | —SO₂—(2,3,5-trimethyl-6-OCH₃-phenyl) | —(CH₂)₂COOCH(CH₃)₂ | 55 | 776 | 0.37, I(9:1) | 142 114 |
| 34 | —SO₂—(2,3,5-trimethyl-6-OCH₃-phenyl) | -4-C₆H₄—COOC₂H₅ | 59 | 810 | 0.40, I(87:13) | 218 |
| 34a | -4-SO₂—C₆H₄—CH₃ | —CH₂C(CH₃)₂OCH₃ | 67 | 690 | 0.14, I(9:1) | 162 |

The products listed in Table 2 are obtained by hydrolysis of the compounds (starting material) from the examples stated as described for Example 2:

TABLE 2

[Structure: R₄—NH—C(=O)—NH—CH(side chain with guanidine N—SO₂-4-methylphenyl)—C(=O)—NH—CH(isopropyl)—C(=O)—NH—CH(CH₂-phenyl)—CH₂OH]

| Ex. No. | $R^4$ | Yield (% of theory) | MS (FAB) m/z (M + H)⁺ | $R_f$/mobile phase ratio | Melting point: (°C.) | IR γ(cm⁻¹) | Starting material from Example No. |
|---|---|---|---|---|---|---|---|
| 35 | —CH₂—COOH | 83 | 662 | 0.16, III(9:1) | 158 | 1727, 1641, 1551, 1248 | 14 |
| 36 | —CH₂CH₂COOH | 82 | 676 | 0.22, III(9:1) | 157 | 1728, 1621, 1552, 1274 | 15 |

The products listed in Table 3 are obtained by reaction of the corresponding starting materials in anhydrous hydrofluoric acid as described for Example 3:

TABLE 3

[Structure: R_4—NH—CO—NH—CH(CH_2CH_2CH_2NH—C(=NH)NH_2 × HF)—CO—NH—CH(CH(CH_3)_2)—CO—NH—CH(CH_2-C_6H_5)—CH_2OH]

| Ex. No. | $R^4$ | Yield (% of theory) | MS (FAB) m/z (M + H)$^+$ | $R_f$/mobile phase ratio | $[\alpha]_D^{20}$ (c, DMSO) | IR $\gamma$ (cm$^{-1}$) |
|---|---|---|---|---|---|---|
| 37 | —CH$_2$COOH | 93 | 508 | 0.33, III(7:3) | −22.5 (0.96) | 1638, 1560, 1204, 1137 |
| 38 | —CH$_2$COOC$_2$H$_5$ | 97 | 536 | 0.35, III(85:15) | −20.8 (0.596) | 1654, 1560, 1205 |
| 39 | —CH$_2$CH$_2$COOH | 98 | 522 | 0.24, III(7:3) | −18.5 (0.486) | 1654, 1560, 1203 |
| 40 | —CH$_2$CH$_2$COOCH(CH$_3$)$_2$ | 62 | 564 | 0.53, III(7:3) | −16.2 (0.362) | 1655, 1560 1203 |

The compounds listed in Table 4 are obtained by oxidation of the corresponding starting materials with pyridine/SO$_3$ in DMSO and, if appropriate, separation of the diastereomers by chromatography as described for Example 4 and 5:

TABLE 4

[Structure: R$^1$—NH—CH(CH_2CH_2CH_2NH—C(=N—R_2)NH_2)—CO—NH—CH(CH(CH_3)_2)—CO—NH—CH(CH_2-C_6H_5)—CHO]

| Ex. No. | $R^1$ | $R^2$ | Yield (% of theory) | MS (FAB) m/z (M + H)$^+$ | $R_f$/ mobile phase ratio | Diastereomer | Melting point (°C.) |
|---|---|---|---|---|---|---|---|
| 41 | —CO—NH—CH$_2$COOH | H | 27 | 506 | 0.32, III (7:3) | non-polar, polar | 203 |
| 42 | —CO—NH—CH$_2$C(CH$_3$)$_2$OCH$_3$ | -4-SO$_2$C$_6$H$_4$—CH$_3$ | 69 | 688 | 0.30; 0.33, I (9:1) | non-polar, polar | 159 |
| 43 | —CO—NH—(CH$_2$)$_2$COOCH(CH$_3$)$_2$ | -4-SO$_2$—C$_6$H$_4$—CH$_3$ | 27 | 716 | 0.29, I (9:1) | polar | 143[a)] |
| 44 | —CO—NH—(CH$_2$)$_2$COOCH(CH$_3$)$_2$ | -4-SO$_2$—C$_6$H$_4$—CH$_3$ | 37 | 716 | 0.26, I (9:1) | non-polar | 135[b)] |
| 45 | —CO—NH—CH$_2$CH$_2$COOH | -4-SO$_2$—C$_6$H$_4$—CH$_3$ | 44 | 674 | 0.30, III (9:1) | non-polar, polar | — |
| 46 | —CO—NH—CH$_2$CH$_2$COOH | -4-SO$_2$—C$_6$H$_4$—CH$_3$ | 53 | 520 | 0.26, III (7:3) | non-polar, polar | — |
| 47 | —CO—NH—CH$_2$—COOC$_2$H$_5$ | -4-SO$_2$—C$_6$H$_4$—CH$_3$ | 30 | 688 | 0.26, I (9:1) | non-polar | 109 |
| 48 | —CO—NH—CH$_2$—COOC$_2$H$_5$ | -4-SO$_2$—C$_6$H$_4$—CH$_3$ | 23 | 688 | 0.22, I | polar | 124 |

TABLE 4-continued

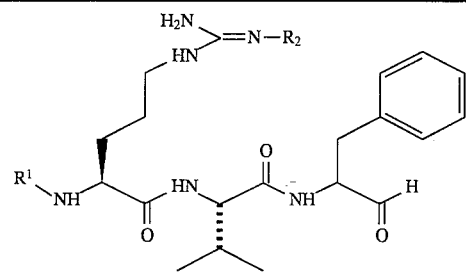

| Ex. No. | R¹ | R² | Yield (% of theory) | MS (FAB) m/z (M + H)⁺ | $R_f$/ mobile phase ratio | Di- aster- eomer | Melting point (°C.) |
|---|---|---|---|---|---|---|---|
| 49 | —CO—NH—(CH₂)₃COOCH₃ | -4-SO₂—C₆H₄—CH₃ | 24 | 702 | 0.29, I (9:1) | non- polar | 134 |
| 50 | —CO—NH—(CH₂)₃COOCH₃ | -4-SO₂—C₆H₄—CH₃ | 21 | 702 | 0.27, I (9:1) | polar | 156 |
| 51 | —CO—NH—(CH₂)₂—COO-n-C₄H₉ | -4-SO₂—C₆H₄—CH₃ | 18 | 730 | 0.20, I (9:1) | non- polar | 122 |
| 52 | —CO—NH—(CH₂)₂—COO-n-C₄H₉ | -4-SO₂—C₆H₄—CH₃ | 23 | 730 | 0.16 I (9:1) | polar | 134 |
| 53 | —CO—NH—(CH₂)₁₁—CH₃ | -4-SO₂—C₆H₄—CH₃ | 20 | 770 | 0.14, I (9:1) | non- polar | 140 |
| 54 | —CO—NH—(CH₂)₁₁—CH₃ | -4-SO₂—C₆H₄—CH₃ | 23 | 770 | 0.11, I (9:1) | polar | 122 |
| 55 | —CO—NH-4-C₆H₄—COOC₂H₅ | -4-SO₂—C₆H₄—CH₃ | 30 | 750 | 0.26, I (9:1) | non- polar | 182 |
| 56 | —CO—NH-4-C₆H₄—COOC₂H₅ | -4-SO₂—C₆H₄—CH₃ | 39 | 750 | 0.21, I (9:1) | polar | 164 |
| 57 | —CO—NH-4-C₆H₄—COCH₃ | -4-SO₂—C₆H₄—CH₃ | 32 | 720 | 0.16, I (9:1) | non- polar | 122 |
| 58 | —CO—NH-4-C₆H₄—COCH₃ | -4-SO₂—C₆H₄—CH₃ | 31 | 720 | 0.14, I (9:1) | polar | 102 |
| 59 | —CO—NH—C(CH₃)₃ | -4-SO₂—C₆H₄—CH₃ | 58 | 658 | 0.21; 0.24, I (9:1) | non- polar, polar | 110 |
| 60 | —CO—NH-3,5-C₆H₃—CO₂CH₃ | -4-SO₂—C₆H₄—CH₃ | 67 | 794 | 0.21; 0.24, I (9:1) | non- polar, polar | 122 |
| 61 | —CO—NH-4-C₆H₄—CF₃ | -4-SO₂—C₆H₄—CH₃ | 63 | 746 | 0.14; 0.17, I (9:1) | non- polar, polar | 165 |
| 62 | —CO—NH-4-C₆H₄—CH=CH—COOC₂H₅ | -4-SO₂—C₆H₄—CH₃ | 83 | 776 | 0.27; 0.29, I (9:1) | non- polar, polar | 128 |
| 63 | —CO—NH-2-C₆H₄—COOC₂H₅ | -4-SO₂—C₆H₄—CH₃ | 76 | 750 | 0.14; 0.18, I (9:1) | non- polar, polar | 115 |
| 64 | —CO—NH-3-C₆H₄—COOC₂H₅ | -4-SO₂—C₆H₄—CH₃ | 49 | 750 | 0.18; 0.22, I (9:1) | non- polar, polar | 136 |
| 65 | —CO—NH-3-C₆H₄—COOCH(CH₃)₂ | -4-SO₂—C₆H₄—CH₃ | 52 | 764 | 0.52; 0.57, I (9:1) | non- polar, polar | 124 |
| 66 | —CO—NH-3-C₆H₄—COOCH₂CH(CH₃)₂ | -4-SO₂—C₆H₄—CH₃ | 85 | 778 | 0.38; 0.44, I (9:1) | non- polar, polar | 108 |
| 67 | —CO—NH-3-C₆H₄—COO(CH₂)₃CH₃ | -4-SO₂—C₆H₄—CH₃ | 84 | 778 | 0.24; 0.28, I (9:1) | non- polar, polar | 106 |
| 68 | —CO—NH-4-C₆H₄—COO(CH₂)₃CH₃ | -4-SO₂—C₆H₄—CH₃ | 85 | 778 | 0.23; 0.32, I (9:1) | | — |
| 69 | Boc | -4-SO₂—C₆H₄—CH₃ | 31 | 659 | 0.26, I (9:1) | unpolar | 138 |
| 70 | Boc | -4-SO₂—C₆H₄—CH₃ | 53 | 659 | 0.24, I (9:1) | polar | Foam |

TABLE 4-continued

| Ex. No. | R¹ | R² | Yield (% of theory) | MS (FAB) m/z (M + H)⁺ | $R_f$/ mobile phase ratio | Di-astereomer | Melting point (°C.) |
|---|---|---|---|---|---|---|---|
| 71 | Fmoc— | —SO₂—(2,6-dimethyl-4-(2,2-dimethylpropyl)phenoxy aryl) | 10 | 893 | 0.30, I (95:5) | unpolar | 131 |
| 72 | Fmoc— | —SO₂—(2,6-dimethyl-4-(2,2-dimethylpropyl)phenoxy aryl) | 5 | 893 | 0.22, I (95:5) | polar | 132 |
| 73 | Fmoc— | —SO₂—(2,6-dimethyl-4-OCH₃ aryl) | 11 | 839 | 0.39, I (85:15) | unpolar | 153 |
| 74 | Fmoc— | —SO₂—(2,6-dimethyl-4-OCH₃ aryl) | 10 | 839 | 0.33, I (85:15) | polar | 92 |
| 75 | PhCH₂OCO— | -4-SO₂—C₆H₄—CH₃ | 65 | 693 | 0.44; 0.52, I (9:1) | unpolar, polar | Oil |
| 76 | —CO—NH—(CH₂)₂COOCH(CH₃)₂ | —SO₂—(2,6-dimethyl-4-(2,2-dimethylpropyl)phenoxy aryl) | 70 | 828 | 0.17; 0.24, I (87:13) | non-polar, polar | 142 |
| 77 | —CO—NH-4-C₆H₄—COOC₂H₅ | —SO₂—(2,6-dimethyl-4-(2,2-dimethylpropyl)phenoxy aryl) | 79 | 862 | 0.22; 0.26, I (9:1) | non-polar, polar | 114 |
| 78 | —CO—NH—CH₂)₂COOCH(CH₃)₂ | —SO₂—(2,6-dimethyl-4-OCH₃ aryl) | 64 | 775 | 0.24; 0.26, I (87:13) | non-polar, polar | 153 |

TABLE 4-continued

[Structure: peptide with guanidino group H2N-C(=NR2)-NH-, ornithine-like residue with R1-NH, valine, and phenylalaninal aldehyde]

| Ex. No. | R¹ | R² | Yield (% of theory) | MS (FAB) m/z (M + H)⁺ | R_f/mobile phase ratio | Di-astereomer | Melting point (°C.) |
|---|---|---|---|---|---|---|---|
| 79 | —CO—NH-4-C₆H₄—COOC₂H₅ | —SO₂—(2,6-dimethyl-4-methoxyphenyl) | 79 | 808 | 0.18; 0.22, I (9:1) | non-polar, polar | 138 |
| 80 | CH₃CO— | —SO₂—C₆H₄—CH₃ | 59 | 601 | 0.26; 0.30, I (9:1) | non-polar, polar | 104 |
| 81 | —CO—NH—CH₂—C(CH₃)₂OCH₃ | —SO₂—C₆H₄—CH₃ | 69 | 688 | 0.30; 0.33, I (9:1) | non-polar, polar | 159 |

ª⁾less polar Isomer: $[\alpha]_D^{20} = 19.5°$ (c = 0.85, DMSO)
ᵇ⁾more polar Isomer: $[\alpha]_D^{20} = -16.4°$ (c = 0.85, DMSO)

The compounds listed in Table 5 are obtained by condensation of the compound from Example III with the corresponding S-arginine derivative as described for Example IV:

TABLE 5

[Structure: analogous peptide with terminal —CH₂OH instead of aldehyde]

| Ex. No. | R² | R¹ | Yield (% of theory) | MS (FAB) m/z (M + H)⁺ | R_f/mobile phase ratio | Melting point (°C.) |
|---|---|---|---|---|---|---|
| 82 | -4-SO₂—C₆H₄—CH₃ | Ph—CH₂—O—CO | 50 | 695 | 0.34., I (9:1) | 110 |
| 83 | —SO₂—(2,6-dimethyl-4-(2,2-dimethyl)ethoxyphenyl) | Fmoc | 57 | 895 | 0.35, II (0:10) | 138 |

TABLE 5-continued

| Ex. No. | R² | R¹ | Yield (% of theory) | MS (FAB) m/z (M + H)⁺ | $R_f$/mobile phase ratio | Melting point (°C.) |
|---|---|---|---|---|---|---|
| 84 | (2,5-dimethyl-4-methoxyphenylsulphonyl) | Fmoc | 55 | 841 | 0.58, I (85:15) | 179 |

EXAMPLE 85

(2S)-2-[N$_\alpha$-Acetyl-N$^G$-(4-methyl-phenylsulphonyl)-S-arginyl-S-valinyl]-amino-3-phenyl-propan-1-ol

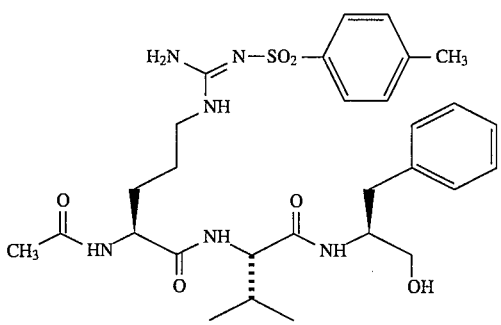

180 μl (1.86 mmol) of acetic anhydride are added dropwise to a solution, cooled to 0° C., of 951 mg (150 mmol) of the compound from Example V in 6 ml of anhydrous dimethylformamide and 660 μl (6.00 mmol) of N-methylmorpholine. After 15 minutes at 0° C. the mixture is poured into a mixture of 120 ml of ice-cold sodium bicarbonate solution and 60 ml of ethyl acetate and the resulting mixture is stirred thoroughly. The organic phase is separated off, the aqueous phase is extracted with 10 ml of ethyl acetate and the combined organic extracts are dried over magnesium sulphate. After the solvent has been evaporated off, the residue is crystallized by titration in 10 ml of methylene chloride and 50 ml of ether. 532 mg (59%) of the title compound are obtained as colourless crystals.

Melting point: 160°–162° C. R$_f$=0.10 methylene chloride:methanol 9:1. MS (FAB) m/z=603 (M+H)⁺.

We claim:

1. A pseudopeptide of formula

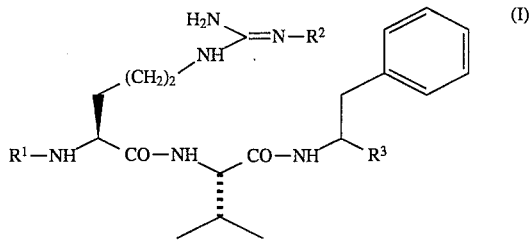

in which

R¹ represents an amino-protective group or represents a radical of the formula R⁴—NH—CO—, wherein R⁴ denotes cycloalkyl having 3 to 6 carbon atoms, or denotes straight-chain or branched alkyl having up to 18 carbon atoms, which is optionally substituted by hydroxyl, straight-chain or branched alkoxy having up to 4 carbon atoms, halogen, trifluoromethyl, trifluoromethoxy, cycloalkyl having 3 to 6 carbon atoms or by aryl having 6 to 10 carbon atoms, which can in turn be substituted up to twice in an identical or different manner by carboxyl, cyano, hydroxyl, halogen, perhalogenoalkyl having up to 5 carbon atoms or by straight-chain or branched acyl, alkoxy or alkoxycarbonyl having in each case up to 6 carbon atoms, or alkyl is optionally substituted by a group of the formula —CO$_2$R⁵, wherein R⁵ denotes hydrogen or straight-chain or branched alkyl or alkenyl having in each case up to 8 carbon atoms, which are optionally substituted by phenyl, or R⁴ denotes aryl having 6 to 10 carbon atoms, which is optionally substituted up to 3 times in an identical or different manner by carboxyl, halogen, hydroxyl, cyano, perhalogenoalkyl having up to 5 carbon atoms or by straight-chain or branched acyl, alkoxy, alkoxycarbonyl or vinylalkoxycarbonyl having in each case up to 6 carbon atoms, or denotes an amino acid radical of the formula

wherein
$R^6$ and $R^7$ are identical or different and denote hydrogen or methyl, or
$R^6$ and $R^7$ together form a 5- or 6-membered saturated carbocyclic ring,
or
$R^6$ denotes hydrogen or methyl
and
$R^7$ denotes cycloalkyl having 3 to 8 carbon atoms or aryl having 6 to 10 carbon atoms or hydrogen, or denotes straight-chain or branched alkyl having up to 8 carbon atoms, the alkyl optionally being substituted by methylthio, hydroxyl, mercapto, guanidyl or by a group of the formula —$NR^9R^{10}$ or $R^{11}$—OC—,
wherein
$R^9$ and $R^{10}$ independently of one another represent hydrogen, straight-chain or branched alkyl having up to 8 carbon atoms or phenyl,
and
$R^{11}$ denotes hydroxyl, benzyloxy, alkoxy having up to 6 carbon atoms or the abovementioned group —$NR^9R^{10}$,
or the alkyl is optionally substituted by cycloalkyl having 3 to 8 carbon atoms or by aryl having 6 to 10 carbon atoms, which is in turn substituted by hydroxyl, halogen, nitro, alkoxy having up to 8 carbon atoms or by the group —$NR^9R^{10}$,
wherein
$R^9$ and $R^{10}$ have the abovementioned meaning,
or the alkyl is optionally substituted by a 5- to 6-membered nitrogen-containing heterocycle or indolyl, wherein the corresponding —NH— functions are optionally protected by alkyl having up to 6 carbon atoms or by an amino-protective group,
$R^8$ denotes straight-chain or branched alkyl having up to 8 carbon atoms, which is optionally substituted by hydroxyl or straight-chain or branched alkoxy having up to 6 carbon atoms, or
denotes carboxyl, allyloxycarbonyl, straight-chain or branched alkoxycarbonyl having up to 8 carbon atoms or benzyloxycarbonyl,
$R^2$ represents a radical of the formula —$SO_2$—$R^{12}$,
wherein
$R^{12}$ denotes methyl or phenyl, which is optionally substituted up to 4 times in an identical or different manner by methyl or methoxy, or denotes a radical of the formula

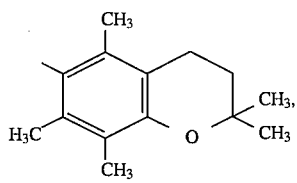

$R^3$ represents formyl or carboxyl or represents straight-chain or branched alkoxycarbonyl having up to 8 carbon atoms or represents a radical of the formula —$CH_2$—$OR^{13}$ or —$CH(OR^{14})_2$,
wherein $R^{13}$ and $R^{14}$ are identical or different and denote hydrogen, straight-chain or branched alkyl having up to 6 carbon atoms or a hydroxyl-protective group,
if appropriate in an isomeric form, or a salt thereof.

2. A compound according to claim 1,
in which
$R^1$ represents acetyl, tert-butoxycarbonyl (Boc), benzyloxycarbonyl (Z) or 9-fluorenylmethoxycarbonyl (Fmoc), or
represents a radical of the formula $R^4$—NH—CO—,
wherein
$R^4$ denotes cyclopentyl or cyclohexyl or denotes straight-chain or branched alkyl having up to 16 carbon atoms, which is optionally substituted by hydroxyl, methoxy, fluorine, chlorine, bromine, trifluoromethyl, trifluoromethoxy, cyclopentyl, cyclohexyl or phenyl, which can in turn be substituted up to twice in an identical or different manner by carboxyl, cyano, hydroxyl, fluorine, chlorine, bromine, perhalogenoalkyl having up to 4 carbon atoms or by straight-chain or branched acyl, alkoxy or alkoxycarbonyl having in each case up to 4 carbon atoms, or alkyl is optionally substituted by a group of the formula —$CO_2R^5$,
wherein
$R^5$ denotes hydrogen or straight-chain or branched alkyl or alkenyl having in each case up to 6 carbon atoms, which are optionally substituted by phenyl,
or
$R^4$ denotes phenyl or naphthyl, which is optionally substituted up to 3 times in an identical or different manner by carboxyl, fluorine, chlorine, bromine, hydroxyl, cyano, perhalogenoalkyl having up to 4 carbon atoms or by straight-chain or branched acyl, alkoxy, alkoxycarbonyl or vinylalkoxycarbonyl having in each case up to 5 carbon atoms, or denotes an amino acid radical of the formula

wherein
$R^6$ and $R^7$ are identical or different and denote hydrogen or methyl, or
$R^6$ and $R^7$ together form a cyclopentyl or cyclohexyl ring,
or
$R^6$ denotes hydrogen or methyl
and
$R^7$ denotes cyclopentyl, cyclohexyl, phenyl or hydrogen, or denotes straight-chain or branched alkyl having up to 6 carbon atoms, the alkyl optionally being able to be substituted by methylthio, hydroxyl, mercapto, guanidyl, amino, carboxyl or $H_2N$—CO—,
or the alkyl is substituted by cyclohexyl, naphthyl or phenyl, which can in turn be substituted by fluorine, hydroxyl, nitro or alkoxy having up to 4 carbon atoms,
or the alkyl is optionally substituted by indolyl, imidazolyl, pyridyl, triazolyl or pyrazolyl, the corresponding —NH— functions optionally being protected by alkyl having up to 4 carbon atoms or by an amino-protective group,
$R^8$ denotes straight-chain or branched alkyl having up to 6 carbon atoms, which is optionally substituted by hydroxyl or straight-chain or branched alkoxy having up to 4 carbon atoms, or denotes carboxyl, allyloxycarbonyl, straight-chain or branched alkoxycarbonyl having up to 6 carbon atoms or benzyloxycarbonyl, $R^2$ represents a radical of the formula $-SO_2-R^{12}$, wherein $R^{12}$ denotes methyl or phenyl, which is optionally substituted up to 4 times in an identical or different manner by methyl or methoxy, or denotes a radical of the formula

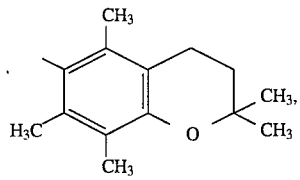

$R^3$ represents formyl or carboxyl or represents straight-chain or branched alkoxycarbonyl having up to 6 carbon atoms, or represents a radical of the formula $-CH_2-OR^{13}$ or $-CH(OR^{14})_2$, wherein $R^{13}$ and $R^{14}$ are identical or different and denote hydrogen, straight-chain or branched alkyl having up to 4 carbon atoms, acetyl or benzyl, if appropriate in an isomeric form, or a salt thereof.

3. A compound according to claim 1, in which $R^1$ represents acetyl, tert-butoxycarbonyl (Boc), benzyloxycarbonyl (Z) or 9-fluorenylmethoxycarbonyl (Fmoc), or represents a radical of the formula $R^4-NH-CO-$, wherein $R^4$ denotes cyclopentyl or cyclohexyl or denotes straight-chain or branched alkyl having up to 14 carbon atoms, which is optionally substituted by hydroxyl, methoxy, fluorine, trifluoromethyl, trifluoromethoxy, cyclohexyl or phenyl, or which is optionally substituted by a group of the formula $-CO_2R^5$, wherein $R^5$ denotes hydrogen or straight-chain or branched alkyl or alkenyl having in each case up to 4 carbon atoms or benzyl, or $R^4$ denotes phenyl, which is optionally substituted up to twice in an identical or different manner by carboxyl, fluorine, hydroxyl, cyano, trifluoromethyl or by straight-chain or branched acyl, alkoxy, alkoxycarbonyl or vinylalkoxycarbonyl having in each case up to 4 carbon atoms, or denotes an amino acid radical of the formula

wherein $R^6$ and $R^7$ are identical or different and denote hydrogen or methyl, or $R^6$ and $R^7$ together form a cyclohexyl ring, or $R^6$ denotes hydrogen or methyl and $R^7$ denotes cyclopentyl, cyclohexyl or hydrogen, or denotes straight-chain or branched alkyl having up to 4 carbon atoms, the alkyl optionally being able to be substituted by methylthio, hydroxyl, mercapto, guanidyl, amino, carboxyl or $H_2N-CO-$, or the alkyl is substituted by cyclohexyl, naphthyl or phenyl, which can in turn be substituted by fluorine, chlorine or alkoxy having up to 4 carbon atoms, or the alkyl is optionally substituted by imidazolyl, pyridyl or pyrazolyl, the corresponding $-NH-$ functions optionally being protected by methyl, benzyloxymethylene or tert-butyloxycarbonyl (Boc), $R^8$ denotes straight-chain or branched alkyl having up to 4 carbon atoms, which is optionally substituted by hydroxyl or straight-chain or branched alkoxy having up to 3 carbon atoms, or denotes carboxyl, allyloxycarbonyl, straight-chain or branched alkoxycarbonyl having up to 4 carbon atoms or benzyloxycarbonyl, $R^2$ represents a radical of the formula $-SO_2-R^{12}$, wherein $R^{12}$ denotes methyl or phenyl, which is optionally substituted up to 4 times in an identical or different manner by methyl or methoxy, or denotes a radical of the formula

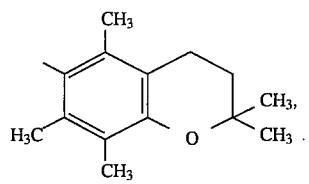

$R^3$ represents formyl or carboxyl or represents straight-chain or branched alkoxycarbonyl having up to 4 carbon atoms, or represents a radical of the formula $-CH_2-OR^{13}$ or $-CH(OR^{14})_2$, wherein $R^{13}$ and $R^{14}$ are identical or different and denote hydrogen, straight-chain or branched alkyl having up to 3 carbon atoms or benzyl, if appropriate in an isomeric form, or a salt thereof.

4. A process for the preparation of the compound of the formula (I) according to claim 1, characterized in that compounds of the formula (III)

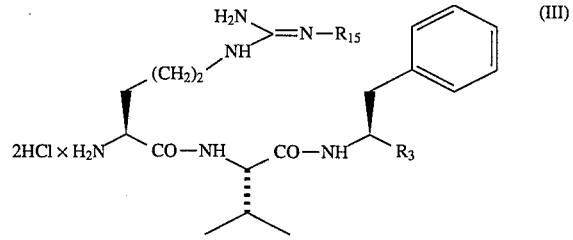

in which $R^3$ has the abovementioned meaning and $R^{15}$ has the abovementioned meaning of $R^2$, but does not represent hydrogen, are first converted, by reaction with compounds of the general formula (IV)

$R^4-N=C=O$           (IV)

in which $R^4$ has the abovementioned meaning,
in inert solvents, in the presence of a base, into the compounds of the general formula (V)

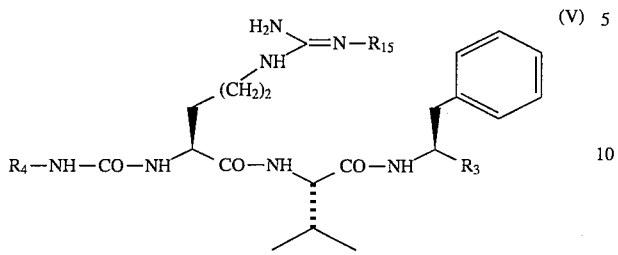

in which $R^3$, $R^4$ and $R^{15}$ have the abovementioned meaning,
and, in the case where $R^3$=CH$_2$—OH, the compounds of the general formula ($R^3$=—CO$_2$CH$_3$) (V) are reacted by customary methods, but preferably with sodium borohydride, and, in the case where $R^3$=CHO, the compounds of the general formula (V) are subjected to a Swern oxidation, starting from the hydroxymethyl compound ($R^3$=CH$_2$—OH),
and, depending on the radical $R^{15}$, are reacted, for example, with hydrofluoric acid or trifluoroacetic acid,
and, in the case of an amino-protective group ($R^1/R^{15}$), this is split off by the methods customary in peptide chemistry, and, in the case of the acids, the esters are hydrolysed.

5. A compound according to claim 1, in which $R^1$ represents an amino-protective group or represents a radical of the formula $R^4$—NH—CO—, wherein $R^4$ denotes cycloalkyl having 3 to 6 carbon atoms, or denotes straight-chain or branched alkyl having up to 18 carbon atoms, which is optionally substituted by hydroxyl, straight-chain or branched alkoxy having up to 4 carbon atoms, halogen, trifluoromethyl, trifluoromethoxy, cycloalkyl having 3 to 6 carbon atoms or by aryl having 6 to 10 carbon atoms, which can in turn be substituted up to twice in an identical or different manner by carboxyl, cyano, hydroxyl, halogen, perhalogenoalkyl having up to 5 carbon atoms or by straight-chain or branched acyl, alkoxy or alkoxycarbonyl having in each case up to 6 carbon atoms, or alkyl is optionally substituted by a group of the formula —CO$_2$R$^5$, wherein $R^5$ denotes hydrogen or straight-chain or branched alkyl or alkenyl having in each case up to 8 carbon atoms, which are optionally substituted by phenyl, or $R^4$ denotes aryl having 6 to 10 carbon atoms, which is optionally substituted up to 3 times in an identical or different manner by carboxyl, halogen, hydroxyl, cyano, perhalogenoalkyl having up to 5 carbon atoms or by straight-chain or branched acyl, alkoxy, alkoxycarbonyl or vinylalkoxycarbonyl having in each case up to 6 carbon atoms, or denotes an amino acid radical of the formula

wherein $R^6$ and $R^7$ are identical or different and denote hydrogen or methyl or $R^6$ denotes hydrogen or methyl and $R^7$ denotes cycloalkyl having 3 to 8 carbon atoms or aryl having 6 to 10 carbon atoms or hydrogen, or denotes straight-chain or branched alkyl having up to 8 carbon atoms, the alkyl optionally being substituted by methylthio, hydroxyl, mercapto, or guanidyl, or the alkyl is optionally substituted by cycloalkyl having 3 to 8 carbon atoms or by aryl having 6 to 10 carbon atoms, which is in turn substituted by hydroxyl, halogen, nitro, or alkoxy having up to 8 carbon atoms, $R^8$ denotes straight-chain or branched alkyl having up to 8 carbon atoms, which is optionally substituted by hydroxyl or straight-chain or branched alkoxy having up to 6 carbon atoms, or denotes carboxyl, allyloxycarbonyl, straight-chain or branched alkoxycarbonyl having up to 8 carbon atoms or benzyloxycarbonyl, $R^2$ represents a radical of the formula —SO$_2$—R$^{12}$, wherein $R^{12}$ denotes methyl or phenyl, which is optionally substituted up to 4 times in an identical or different manner by methyl or methoxy, or denotes a radical of the formula

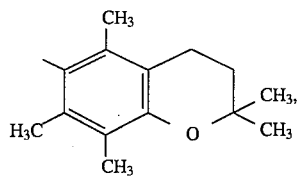

$R^3$ represents formyl or carboxyl or represents straight-chain or branched alkoxycarbonyl having up to 8 carbon atoms or represents a radical of the formula —CH$_2$—OR$^{13}$ or —CH(OR$^{14}$)$_2$, wherein $R^{13}$ and $R^{14}$ are identical or different and denote hydrogen, straight-chain or branched alkyl having up to 6 carbon atoms or a hydroxyl-protective group, if appropriate in an isomeric form, or a salt thereof.

6. A compound according to claim 1, in which $R^1$ represents acetyl, tert-butoxycarbonyl (Boc), benzyloxycarbonyl (Z) or 9-fluorenylmethoxycarbonyl (Fmoc), or represents a radical of the formula $R^4$—NH—CO—, wherein $R^4$ denotes cyclopentyl or cyclohexyl or denotes straight-chain or branched alkyl having up to 16 carbon atoms, which is optionally substituted by hydroxyl, methoxy, fluorine, chlorine, bromine, trifluoromethyl, trifluoromethoxy, cyclopentyl, cyclohexyl or phenyl, which can in turn be substituted up to twice in an identical or different manner by carboxyl, cyano, hydroxyl, fluorine, chlorine, bromine, perhalogenoalkyl having up to 4 carbon atoms or by straight-chain or branched acyl, alkoxy or alkoxycarbonyl having in each case up to 4 carbon atoms, or alkyl is optionally substituted by a group of the formula —$CO_2R^5$, wherein $R^5$ denotes hydrogen or straight-chain or branched alkyl or alkenyl having in each case up to 6 carbon atoms, which are optionally substituted by phenyl, or $R^4$ denotes phenyl or naphthyl, which is optionally substituted up to 3 times in an identical or different manner by carboxyl, fluorine, chlorine, bromine, hydroxyl, cyano, perhalogenoalkyl having up to 4 carbon atoms or by straight-chain or branched acyl, alkoxy, alkoxycarbonyl or vinylalkoxycarbonyl having in each case up to 5 carbon atoms, or denotes an amino acid radical of the formula

wherein $R^6$ and $R^7$ are identical or different and denote hydrogen or methyl, or or $R^6$ denotes hydrogen or methyl and $R^7$ denotes cyclopentyl, cyclohexyl, phenyl or hydrogen, or denotes straight-chain or branched alkyl having up to 6 carbon atoms, the alkyl optionally being able to be substituted by methylthio, hydroxyl, mercapto, guanidyl, amino, carboxyl or $H_2N$—CO—, or the alkyl is substituted by cyclohexyl, naphthyl or phenyl, which can in turn be substituted by fluorine, hydroxyl, nitro or alkoxy having up to 4 carbon atoms, $R^8$ denotes straight-chain or branched alkyl having up to 6 carbon atoms, which is optionally substituted by hydroxyl or straight-chain or branched alkoxy having up to 4 carbon atoms, or denotes carboxyl, allyloxycarbonyl, straight-chain or branched alkoxycarbonyl having up to 6 carbon atoms or benzyloxycarbonyl, $R^2$ represents a radical of the formula —$SO_2$—$R^{12}$, wherein $R^{12}$ denotes methyl or phenyl, which is optionally substituted up to 4 times in an identical or different manner by methyl or methoxy, or denotes a radical of the formula

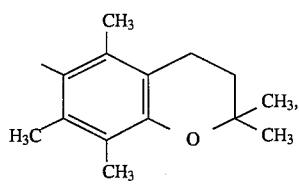

$R^3$ represents formyl or carboxyl or represents straight-chain or branched alkoxycarbonyl having up to 6 carbon atoms, or represents a radical of the formula —$CH_2$—$OR^{13}$ or —$CH(OR^{14})_2$, wherein $R^{13}$ and $R^{14}$ are identical or different and denote hydrogen, straight-chain or branched alkyl having up to 4 carbon atoms, acetyl or benzyl, if appropriate in an isomeric form, or a salt thereof.

7. A compound according to claim 1, in which $R^1$ represents acetyl, tert-butoxycarbonyl (Boo), benzyloxycarbonyl (Z) or 9-fluorenylmethoxycarbonyl (Fmoc), or represents a radical of the formula $R^4$—NH—CO—, wherein $R^4$ denotes cyclopentyl or cyclohexyl or denotes straight-chain or branched alkyl having up to 14 carbon atoms, which is optionally substituted by hydroxyl, methoxy, fluorine, trifluoromethyl, trifluoromethoxy, cyclohexyl or phenyl, or which is optionally substituted by a group of the formula —$CO_2R^5$, wherein $R^5$ denotes hydrogen or straight-chain or branched alkyl or alkenyl having in each case up to 4 carbon atoms or benzyl, or $R^4$ denotes phenyl, which is optionally substituted up to twice in an identical or different manner by carboxyl, fluorine, hydroxyl, cyano, trifluoromethyl or by straight-chain or branched acyl, alkoxy, alkoxycarbonyl or vinylalkoxycarbonyl having in each case up to 4 carbon atoms, or denotes an amino acid radical of the formula

wherein $R^6$ and $R^7$ are identical or different and denote hydrogen or methyl, or $R^6$ denotes hydrogen or methyl and $R^7$ denotes cyclopentyl, cyclohexyl or hydrogen, or denotes straight-chain or branched alkyl having up to 4 carbon atoms, the alkyl optionally being able to be substituted by methylthio, hydroxyl, mercapto, guanidyl, amino, carboxyl or $H_2N$—CO—, or the alkyl is substituted by cyclohexyl, naphthyl or phenyl, which can in turn be substituted by fluorine, chlorine or alkoxy having up to 4 carbon atoms, $R^8$ denotes straight-chain or branched alkyl having up to 4 carbon atoms, which is optionally substituted by hydroxyl or straight-chain or branched alkoxy having up to 3 carbon atoms, or denotes carboxyl, allyloxycarbonyl, straight-chain or branched alkoxycarbonyl having up to 4 carbon atoms or benzyloxycarbonyl, $R^2$ represents a radical of the formula —$SO_2$—$R^{12}$, wherein $R^{12}$ denotes methyl or phenyl, which is optionally substituted up to 4 times in an identical or different manner by methyl or methoxy, or denotes a radical of the formula

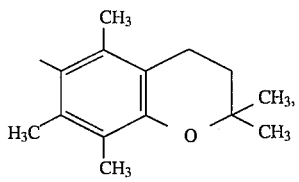

R$^3$ represents formyl or carboxyl or represents straight-chain or branched alkoxycarbonyl having up to 4 carbon atoms, or represents a radical of the formula —CH$_2$—OR$^{13}$ or —CH(OR$^{14}$)$_2$, wherein R$^{13}$ and R$^{14}$ are identical or different and denote hydrogen, straight-chain or branched alkyl having up to 3 carbon atoms or benzyl, if appropriate in an isomeric form, or a salt thereof.

8. A composition comprising an effective amount of a compound according to claim 1 and an inert carrier.

9. A method of treating cytomegalovirus infections which comprises administering at least one of a compound according to claim 1 to host in need thereof.

* * * * *